(12) United States Patent
Deutzmann et al.

(10) Patent No.: US 10,494,596 B2
(45) Date of Patent: Dec. 3, 2019

(54) ENHANCED MICROBIAL ELECTROSYNTHESIS BY USING CO-CULTURES

(71) Applicant: The Board of Trustees of the Leland Stanford Junior University, Stanford, CA (US)

(72) Inventors: Joerg S. Deutzmann, East Palo Alto, CA (US); Alfred Michael Spormann, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 121 days.

(21) Appl. No.: 15/374,949

(22) Filed: Dec. 9, 2016

(65) Prior Publication Data

US 2017/0166883 A1 Jun. 15, 2017

Related U.S. Application Data

(60) Provisional application No. 62/264,990, filed on Dec. 9, 2015.

(51) Int. Cl.

| | |
|---|---|
| *C12M 1/42* | (2006.01) |
| *C12P 7/54* | (2006.01) |
| *C12P 5/02* | (2006.01) |
| *C12P 7/04* | (2006.01) |
| *C12M 1/12* | (2006.01) |
| *C12P 3/00* | (2006.01) |
| *C12P 7/40* | (2006.01) |

(52) U.S. Cl.
CPC ............ *C12M 35/08* (2013.01); *C12M 25/08* (2013.01); *C12M 35/02* (2013.01); *C12P 3/00* (2013.01); *C12P 5/023* (2013.01); *C12P 7/04* (2013.01); *C12P 7/40* (2013.01); *C12P 7/54* (2013.01); *Y02E 50/343* (2013.01)

(58) Field of Classification Search
None
See application file for complete search history.

(56) References Cited

U.S. PATENT DOCUMENTS

| 8,377,665 B2 | 2/2013 | Barker et al. |
| 2009/0317882 A1 | 12/2009 | Cheng et al. |
| 2011/0177564 A1 | 7/2011 | Stephanopoulos et al. |
| 2013/0256149 A1 | 10/2013 | Popat et al. |
| 2015/0259669 A1 | 9/2015 | May |
| 2016/0312167 A1 | 10/2016 | Harnisch et al. |

FOREIGN PATENT DOCUMENTS

WO 2011087821 A2 7/2011

OTHER PUBLICATIONS

Marshall et al.,"Metabolic Reconstruction and Modeling Microbial Electrosynthesis", Scientific Reports 7, Article No. 8391 pp. 1-12. (2017) (Year: 2017).*
Lohner et al. (2014) Hydrogenase-independent uptake and metabolism of electrons by the archaeon Methanococcus maripaludis. ISME J. 8(8):1673-1681.
Lovley (2011) Powering microbes with electricity: direct electron transfer from electrodes to microbes. Environmental Microbiology Reports 3(1):27-35.
Rotaru et al. (2014) Direct interspecies electron transfer between Geobacter metallireducens and Methanosarcina barkeri. Appl. Environ. Microbiol. 80(15):4599-4605.
Kato et al. (2012) Microbial interspecies electron transfer via electric currents through conductive minerals. Proc. Natl. Acad. Sci. USA 109:10042-10046.
Croese et al. (2011) Analysis of the microbial community of the biocathode of a hydrogen-producing microbial electrolysis cell. Appl. Microbiol. Biotechnol. 92:1083-1093.
Aulenta et al. (2012) Linking bacterial metabolism to graphite cathodes: electrochemical insights into the H2-producing capability of *Desulfovibrio* sp. Chemsuschem. 5:1080-1085.
Nakamura et al. (2010) Electrical current generation across a black smoker chimney. Angew Chem. Int. Ed. Engl. 49:7692-7694.
Jafary et al. (2015) Biocathode in microbial electrolysis cell; present status and future prospects. Renew. Sust. Energ. Rev. 47:23-33.
Geelhoed et al. (2010) Electricity-mediated biological hydrogen production. Curr. Opin. Microbiol. 13:307-315.
Kim et al. (2015) The biocathode of microbial electrochemical systems and microbially-influenced corrosion. Bioresour Technol. 190:395-401.
Cheng et al. (2009) Direct biological conversion of electrical current into methane by electromethanogenesis. Environ. Sci. Technol. 43:3953-3958.
Siegert et al. (2015) Methanobacterium Dominates Biocathodic Archaeal Communities in Methanogenic Microbial Electrolysis Cells. ACS Sustain. Chem. Eng. 3:1668-1676.
Beese-Vasbender et al. (2015) Selective microbial electrosynthesis of methane by a pure culture of a marine lithoautotrophic archaeon. Bioelectrochemistry 102:50-55.
Nevin et al. (2010) Microbial electrosynthesis: feeding microbes electricity to convert carbon dioxide and water to multicarbon extracellular organic compounds. MBio 1:e00103-e00110.
Nevin et al. (2011) Electrosynthesis of organic compounds from carbon dioxide is catalyzed by a diversity of acetogenic microorganisms. Appl. Environ. Microbiol. 77:2882-2886.
Deutzmann et al. (2015) Extracellular enzymes facilitate electron uptake in biocorrosion and bioelectrosynthesis. Mbio 6:e00496-15.
Blanchet et al. (2015) Importance of the hydrogen route in up-scaling electrosynthesis for microbial CO2 reduction. Energ. Environ. Sci. 8:3731-3744.

(Continued)

*Primary Examiner* — Anand U Desai
(74) *Attorney, Agent, or Firm* — Jenny J. Buchbinder; Bozicevic, Field & Francis LLP

(57) ABSTRACT

A method of microbial electrosynthesis using co-cultures is disclosed. In particular, the invention relates to a method of microbial electrosynthesis utilizing a microbial strain capable of electron uptake from an electrode to produce hydrogen or formate in co-culture with a microbial production strain, such as a methanogen, acetogen, or other microorganism capable of synthesizing valuable products from carbon dioxide and hydrogen or formate.

34 Claims, 27 Drawing Sheets

(56) References Cited

OTHER PUBLICATIONS

Villano et al. (2010) Bioelectrochemical reduction of CO(2) to CH(4) via direct and indirect extracellular electron transfer by a hydrogenophilic methanogenic culture. Bioresour. Technol. 101:3085-3090.

Rosenbauma et al. (2011) Cathodes as electron donors for microbial metabolism: Which extracellular electron transfer mechanisms are involved? Bioresour. Technol. 102(1):324-333.

Yates et al. (2014) Hydrogen evolution catalyzed by viable and non-viable cells on biocathodes. Int. J. Hydrogen Energ. 39:16841-16851.

Dinh et al. (2004) Iron corrosion by novel anaerobic microorganisms. Nature 427:829-832.

Enning et al. (2012) Marine sulfate-reducing bacteria cause serious corrosion of iron under electroconductive biogenic mineral crust. Environ. Microbiol. 14:1772-1787.

Venzlaff et al. (2013) Accelerated cathodic reaction in microbial corrosion of iron due to direct electron uptake by sulfate-reducing bacteria. Corros. Sci. 66:88-96.

Beese-Vasbender et al. (2015) Electrochemical characterization of direct electron uptake in electrical microbially influenced corrosion of iron by the lithoautotrophic SRB Desulfopila corrodens strain IS4. Electrochimica Acta 167:321-329.

Cord-Ruwisch et al. (1998) Growth of Geobacter sulfurreducens with acetate in syntrophic cooperation with hydrogen-oxidizing anaerobic partners. Appl Environ Microbiol 64: 2232-2236.

Ganigue et al. (2015) Microbial electrosynthesis of butyrate from carbon dioxide. Chem. Commun. 51: 3235-3238.

Kopke et al. (2010) Clostridium Ijungdahlii represents a microbial production platform based on syngas. Proc. Natl. Acad. Sci. USA 107:13087-13092.

Leang et al. (2013) Clostridium Ijungdahlii represents a microbial production platform based on syngas. Environ. Microbiol. 79:1102-1109.

Banerjee et al. (2014) Lactose-inducible system for metabolic engineering of Clostridium Ijungdahlii. Appl. Environ. Microbiol. 80:2410-2416.

Cho et al. (2015) Metabolic engineering of clostridia for the production of chemicals. Biofuels, Bioprod. Biorefin. 9:211-225.

Diender et al. (2016) Production of medium-chain fatty acids and higher alcohols by a synthetic co-culture grown on carbon monoxide or syngas. Biotechnol Biofuels. 9:82.

Lu et al. (2015) Graphene oxide and H2 production from bioelectrochemical graphite oxidation. Sci Rep. 17;5:16242.

Nevin et al. (2008) Power output and columbic efficiencies from biofilms of Geobacter sulfurreducens comparable to mixed community microbial fuel cells. Environ. Microbiol. 10:2505-2514.

Call et al. (2009) Hydrogen production by geobacter species and a mixed consortium in a microbial electrolysis cell. Appl. Environ. Microbiol. 75:7579-7587.

Uchiyama et al. (2010) Iron-corroding methanogen isolated from a crude-oil storage tank. Appl. Environ. Microbiol 76:1783-1788.

Marshall et al. (2012) Electrosynthesis of commodity chemicals by an autotrophic microbial community. Appl. Environ. Microbiol. 78:8412-8420.

Marshall et al. (2013) Long-term operation of microbial electrosynthesis systems improves acetate production by autotrophic microbiomes. Environ. Sci. Technol. 47:6023-6029.

Labelle et al. (2014) Influence of acidic pH on hydrogen and acetate production by an electrosynthetic microbiome. PloS One 9:e109935.

Patil et al. (2015) Selective Enrichment Establishes a Stable Performing Community for Microbial Electrosynthesis of Acetate from $CO_2$. Environ. Sci. Technol. 49:8833-8843.

\* cited by examiner

ENHANCED MICROBIAL ELECTROSYNTHESIS BY USING CO-CULTURES

TECHNICAL FIELD

The present invention relates to production of organic compounds and biofuels by microbial electrosynthesis. In particular, the invention relates to a method of microbial electrosynthesis utilizing a first microorganism capable of electron uptake from an electrode in co-culture with a second microorganism capable of biosynthesis of a compound of interest by reduction of carbon dioxide via interspecies electron transfer.

BACKGROUND

Microbial metabolism of electrons that are not associated with a chemical element, that is, 'free' electrons, is an intriguing metabolic capacity that has been primarily investigated in insoluble metal-reducing microorganisms, such as *Shewanella* or *Geobacter* species (Bond and Lovley (2003) Appl. Environ. Microbiol. 69:1548-1555; Hartshorne et al. (2009) Proc. Natl. Acad. Sci. USA 106:22169-22174; Coursolle et al. (2010) J. Bacteriol. 192:467-474; Clarke et al. (2011) Proc. Natl. Acad. Sci. USA 108:9384-9389; Lovley (2012) Annu. Rev. Microbiol. 66:391-409; Liu et al. (2014) Environ. Microbiol. Rep. 6:776-785; Malvankar and Lovley (2014) Curr. Opin. Biotechnol. 27C:88-95; Pirbadian et al. (2014) Proc. Natl. Acad. Sci. USA 111:12883-12888; TerAvest et al. (2014) Chemelectrochem. 1:1874-1879. In addition to these anodic microbial processes, recent studies have revealed that some microorganisms can take up 'free' cathodic electrons from conductive minerals during interspecies electron transfer (Kato et al. (2012) Proc. Natl. Acad. Sci. USA 109:10042-10046) or from abiotically reduced surfaces such as deep sea hydrothermal vent chimneys (Nakamura et al. (2010) Angew Chem. Int. Ed. Engl. 49:7692-7694). This use of 'free' electrons as electron donors in microbial catabolism also finds relevance in engineered bioelectrochemical systems, which have been emerging as promising platforms for a sustainable energy landscape. In particular, biocathodes in microbial electrosynthesis reactors are of interest, where microorganisms at the cathode convert electricity plus $CO_2$ into useful chemical products. From a fundamental perspective, the mechanisms involved in cathodic electron uptake are most intriguing, however, largely unknown.

The most basic biocathode is the hydrogen-evolving bio-cathode. Most studies on hydrogen-evolving bio-cathodes in a microbial electrosynthesis reactor have been carried out using mixed microbial cultures (Jafary et al. (2015) Renew. Sust. Energ. Rev. 47:23-33), and the ecology of the different microorganisms in a community is poorly understood. A few studies showed hydrogen formation by pure cultures of *Geobacter sulfurreducens* (Geelhoed et al. (2010) Curr. Opin. Microbiol. 13:307-315) or *Desulfovibrio* species (Croese et al. (2011) Appl. Microbiol. Biotechnol. 92:1083-1093); Aulenta et al. (2012) Chemsuschem. 5:1080-1085), and the molecular mechanism of the electron uptake reaction in most hydrogen-evolving, biocathodic microorganisms is unknown (Jafary et al., supra).

A more specialized type of biocathode is found in microbial electro-synthesis. In this process, microorganisms convert cathode-derived electrons plus $CO_2$ into organic compounds rather than free molecular hydrogen. Electrosynthetic methane formation has been achieved using mixed cultures (Cheng et al. (2009) Environ. Sci. Technol. 43:3953-3958, Siegert et al. (2015) ACS Sustain. Chem. Eng. 3:1668-1676) or pure strains such as *Methanococcus maripaludis* and *Methanobacterium* sp. (Lohner et al. (2014) ISME J. 8:1673-1681; Beese-Vasbender et al. (2015) Bioelectrochemistry 102:50-55). Multi-carbon compounds such as acetate have been synthesized on biocathodes using a diversity of homoacetogenic strains (Nevin et al. (2010) MBio 1:e00103-e00110, Nevin et al. (2011) Appl. Environ. Microbiol. 77:2882-2886, Deutzmann et al. (2015) Mbio 6:e00496-15).

Low electron transfer rates from the cathode during microbially catalyzed electrosynthesis were generally considered to be limiting the feasibility of this process on a commercial scale (Blanchet et al. (2015) Energ. Environ. Sci. 8:3731-3744). Moreover, overpotentials of 4200 mV had to be applied repeatedly to achieve significant electron transfer rates (Villano et al. (2010) Bioresour. Technol. 101:3085-3090, Aulenta et al. (2012) Chemsuschem. 5:1080-1085). At these low potentials, the electrochemical formation of small reduced molecules as potential electron carriers such as $H_2$, CO or formate at the cathode cannot be excluded (Villano et al., supra; Yates et al. (2014) Int. J. Hydrogen Energ. 39:16841-16851; Deutzmann et al., supra). To our knowledge, all methanogens and homoacetogens studied for their electrosynthetic properties are able to metabolize at least some of these small reduced molecules.

Besides methanogenic archaea and homoacetogenic bacteria, Fe(0)-corroding microorganisms have been intensively investigated for their outstanding electron transfer capabilities (Dinh et al. (2004) Nature 427:829-832; Uchiyama et al. (2010) Appl. Environ. Microbiol. 76:1783-1788; Enning et al. (2012) Environ. Microbiol. 14:1772-1787; Venzlaff et al. (2013) Corros. Sci. 66: 88-96; Enning and Garrelfs (2014) Appl. Environ. Microbiol. 80:1226-1236; Kato et al. (2015) Appl. Environ. Microbiol. 81:67-73; Beese-Vasbender et al. (2015) Electrochimica Acta 167:321-329). Although direct electron uptake has been proposed in these microorganisms, no mechanism has been identified to date (Enning et al. (2012) Environ. Microbiol. 14:1772-1787; Venzlaff et al. (2013) Corros. Sci. 66:88-96; Enning and Garrelfs, supra; Beese-Vasbender et al. (2015) Electrochimica Acta 167:321-329). Recently, Fe(0)-corroding microorganisms, in particular strain IS4 ('*Desulfopila corrodens*', previously named *Desulfobacterium corrodens* (Dinh et al. (2004) Nature 427:829-832), have been investigated in electrode systems, and a direct electron transfer mechanism has been postulated (Venzlaff et al., supra; Beese-Vasbender et al. (2015) Electrochimica Acta 167:321-329).

There remains a need for developing better more efficient methods of utilizing microbial electrosynthesis to produce valuable compounds of economic interest.

SUMMARY

The invention relates to a method of microbial electrosynthesis utilizing microbial strains capable of electron uptake from an electrode to produce $H_2$ or formate in co-culture with microbial production strains, such as methanogens, acetogens, or other microorganisms capable of synthesizing desired organic compounds from carbon dioxide and hydrogen or formate.

In one aspect, the invention includes a microbial electrosynthesis system comprising: a) a cathode; b) an anode; c) a power supply electrically connected to the cathode and the anode; d) a first microorganism attached to the cathode, wherein the first microorganism is capable of accepting electrons from the cathode resulting in reduction of protons to produce hydrogen or reduction of carbon dioxide to produce formate; e) a second microorganism in sufficient proximity to the first microorganism to allow consumption of the hydrogen or the formate generated by the first microorganism, wherein the second microorganism is capable of biosynthesis of an organic compound of interest from carbon dioxide and the hydrogen or the formate generated by the first microorganism; and f) media suitable for growth or metabolic activity of the first microorganism and the second microorganism. The first microorganism or the second microorganism may be a bacterium or an archaeon.

The cathode preferably comprises a biocompatible material, such as, but not limited to, graphite or other conductive carbon material, indium tin oxide (ITO), fluorine-doped tin oxide (FTO), platinum, titanium, silver, or gold, or a metal alloy or an oxide comprising at least one of tin, platinum, titanium, silver, or gold. In one embodiment, the medium exposed area of the electrodes is at least 8 $cm^2$.

In certain embodiments, the microbial electrosynthesis system further comprises a chamber, wherein the second microorganism is inside the chamber. In another embodiment, the anode and the cathode are inside the chamber.

In other embodiments, the microbial electrosynthesis system further comprises a first chamber comprising the cathode and a second chamber comprising the anode. In another embodiment, the first microorganism and the second microorganism are inside the first chamber comprising the cathode. In certain embodiments, the microbial electrosynthesis system further comprises a membrane separating the first chamber and the second chamber. The membrane may allow, for example, proton exchange, cation exchange, or anion exchange between the first chamber and the second chamber. In another embodiment, the membrane is a bipolar membrane (i.e., the membrane generates from the medium protons on the cathode facing side and anions on the anode facing side).

In certain embodiments, the first microorganism is a hydrogen or formate producing microorganism. Exemplary hydrogen or formate producing microorganisms include *Desulfopila* (e.g., *Desulfopila corrodens*), *Geobacter* (e.g., *Geobacter sulfurreducens*), and *Desulfovibrio* (e.g., *Desulfovibrio* sp.) species. In one embodiment, the first microorganism is *Desulfopila corrodens* strain IS4. In another embodiment, the hydrogen producing microorganism has a hydrogenase enzyme. In another embodiment, the formate producing microorganism has a formate dehydrogenase or a formate-hydrogen lyase.

In certain embodiments, the second microorganism is a methanogen. Exemplary methanogens include *Methanococcus maripaludis, Methanocaldococcus jannaschii, Methanobrevibacter ruminantium, Methanothermobacter thermautotrophicus, Methanopyrus kandleri, Methanosphaera stadtmanae, Methanobrevibacter smithii, Methanocella paludicola, Methanocella sp., Methanocaldococcus fervens, Methanocaldococcus infernus, Methanocaldococcus vulcanis, Methanococcus aeolicus, Methanococcus vannielii, Methanococcus voltae, Methanocorpusculum labreanum, Methanoculleus marisnigri, Methanosphaerula palustris,* and *Methanospirillum hungatei.*

In certain embodiments, the second microorganism is an acetogen. Exemplary acetogens include members of the *Acetobacterium* genus of anaerobic, gram-positive bacteria belonging to the Eubacteriaceae family, such as *Acetobacterium woodii, Acetobacterium bakii, Acetobacterium carbinolicum, Acetobacterium dehalogenans, Acetobacterium fimetarium, Acetobacterium malicum, Acetobacterium paludosum, Acetobacterium psammolithicum, Acetobacterium submarinus, Acetobacterium tundrae, Acetobacterium wieringae,* and *Acetobacterium* sp.; acetogenic thermophilic bacteria of the Thermoanaerobacteraceae family, including members of the genus *Moorella*, such as *Moorella thermoacetica*, the genus *Thermoanaerobacter*, such as *Thermoanaerobacter kivui*, and the genus *Thermacetogenium*, such as *Thermacetogenium phaeum*; and members of the *Clostridium* genus of anaerobic gram-positive bacteria, such as *Clostridium ljungdahlii* and *Clostridium autoethanogenum*; and acetogenic archaea of the phylum *Bathyarchaeota*.

In another embodiment, the invention includes a microbial electrosynthesis system comprising: a) a first chamber comprising a cathode; b) a second chamber comprising an anode; c) a power supply electrically connected to the cathode and the anode; d) a hydrogen producing microorganism attached to the cathode, wherein the hydrogen producing microorganism is capable of accepting electrons from the cathode; e) a hydrogenotrophic microorganism in sufficient proximity to the hydrogen producing microorganism to allow consumption of hydrogen generated by the hydrogen producing microorganism, wherein the hydrogenotrophic microorganism is capable of biosynthesis of an organic product of interest from carbon dioxide and the hydrogen generated by the hydrogen producing microorganism; and g) media suitable for growth or metabolic activity of the hydrogen producing microorganism and the hydrogenotrophic microorganism. In one embodiment, the hydrogenotrophic microorganism is grown in the same chamber as the hydrogen producing microorganism. In another embodiment, the first chamber and the second chamber are separated by a membrane (e.g., proton exchange, cation exchange, anion exchange, or bipolar).

In another aspect, the invention includes a method of microbial electrosynthesis comprising: a) cultivating the first microorganism on the cathode in a microbial electrosynthesis system, as described herein; b) applying a voltage with the power supply such that an electron is transferred from the cathode to the first microorganism, wherein the reduction of protons results in formation of the hydrogen or wherein the reduction of carbon dioxide results in formation of the formate by the first microorganism; c) cultivating the second microorganism in sufficient proximity to the first microorganism to allow consumption of the hydrogen or the formate by the second microorganism; and d) providing carbon dioxide to the second microorganism, wherein the second microorganism metabolizes the carbon dioxide and the hydrogen or the formate resulting in production of the organic compound of interest.

The choice of the microorganisms will depend on the organic compound product desired. If the desired product is methane, the first microorganism is co-cultured with a methanogen (e.g., *Methanococcus maripaludis*). If the desired product is acetate, the first microorganism is co-cultured with an acetogen (e.g., *Acetobacterium woodii*). In certain embodiments, the first microorganism is a hydrogen producing microorganism and the second microorganism is a hydrogenotrophic microorganism. In another embodiment, the second microorganism is engineered to produce other desired products from metabolism of the carbon dioxide and hydrogen or formate.

Media may be supplied with a continuous or batch fed system. In another embodiment, supply of the media is controlled to limit cell density of the first microorganism to between about $10^7$ to about $10^8$ cells $cm^{-2}$ on the cathode surface. In another embodiment, the growth media for the first microorganism comprises an electron acceptor (e.g., (e.g., sulfate for sulfate-reducing microorganism, nitrate for nitrate-reducing microorganism, or fumarate for fumarate-reducing microorganism).

In another embodiment, the cathode is at a voltage ranging from about −400 mV to about −500 mV.

In another embodiment, the invention includes a method of microbial electrosynthesis comprising: a) cultivating a hydrogen producing microorganism on a cathode of a microbial electrosynthesis system; b) applying a voltage with the power supply such that an electron is transferred from the cathode to the hydrogen producing microorganism, wherein reduction of a proton results in formation of hydrogen gas by the hydrogen producing microorganism; c) cultivating a hydrogenotrophic microorganism in sufficient proximity to the hydrogen producing microorganism to allow consumption of the hydrogen gas by the hydrogenotrophic microorganism; and d) providing carbon dioxide to the hydrogenotrophic microorganism, wherein the hydrogenotrophic microorganism metabolizes the carbon dioxide and the hydrogen gas resulting in production of a desired organic compound.

In certain embodiments, the hydrogen is generated by the hydrogen producing microorganism at a rate of at least 0.4 pmol cm$^{-2}$ h$^{-1}$. For example, the hydrogen may be generated by the hydrogen producing microorganism at a rate ranging from 4 pmol cm$^{-2}$ h$^{-1}$ to 7 pmol cm$^{-2}$ h$^{-1}$.

In another embodiment, the hydrogen is generated from cathodic electrons at a coulombic efficiency of at least 90%.

In another aspect, the invention includes kits comprising a microbial electrosynthesis system or agents for performing microbial electrosynthesis, as described herein. Such kits may comprise a microbial electrosynthesis reactor and/or one or more microorganisms, such as a microorganism capable of cathodic electron uptake (e.g., hydrogen-producing microorganism or formate-producing microorganism), a microorganism capable of biosynthesis of a compound of interest by reduction of carbon dioxide via interspecies electron transfer (e.g., methanogen or acetogen or other microorganisms capable of synthesizing desired organic compounds), and media suitable for their growth.

These and other embodiments of the subject invention will readily occur to those of skill in the art in view of the disclosure herein.

BRIEF DESCRIPTION OF THE FIGURES

FIG. 1A shows current consumption of strain IS4 (black) and uninoculated control (gray). FIG. 1B shows hydrogen accumulation by strain IS4 (black squares) and uninoculated control (open squares). FIG. 1C shows sulfide accumulation by strain IS4 (gray circles) and control (open circles) and sulfate consumption by strain IS4 (black squares) and control (open squares). For clarity, one representative reactor out of ten replicates (five for controls) is shown. The trend is identical in all replicates, but the onset of current consumption and activity is shifted among the replicates.

*maripaludis* (medium gray) and pure *M. maripaludis* (light grey) after incubation at −400 mV versus SHE. Scanning speed was 1 mV s$^{-1}$. All three replicates for each condition are shown.

Figure 9:
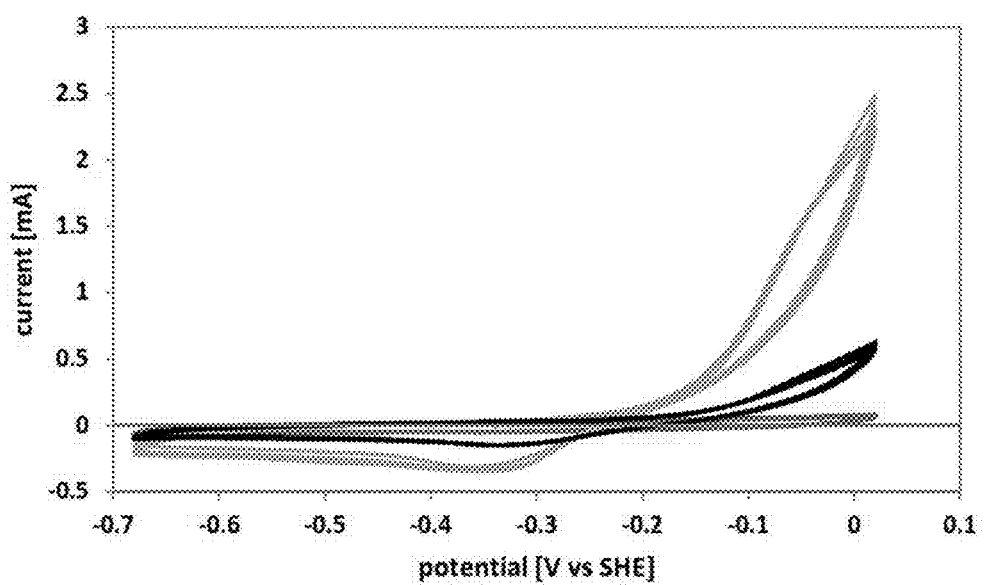

FIG. 9 shows cyclic voltammograms of the catholyte medium without addition (red), with 1 mM sulfide (black) and with 10 mM sulfide (gray) added to the catholyte. A notable anodic current is present at potentials higher than −250 mV, presumably due to oxidation of sulfide. At higher sulfide concentrations, a reduction peak was observed at potentials lower than −250 mV.

Figure 10A:
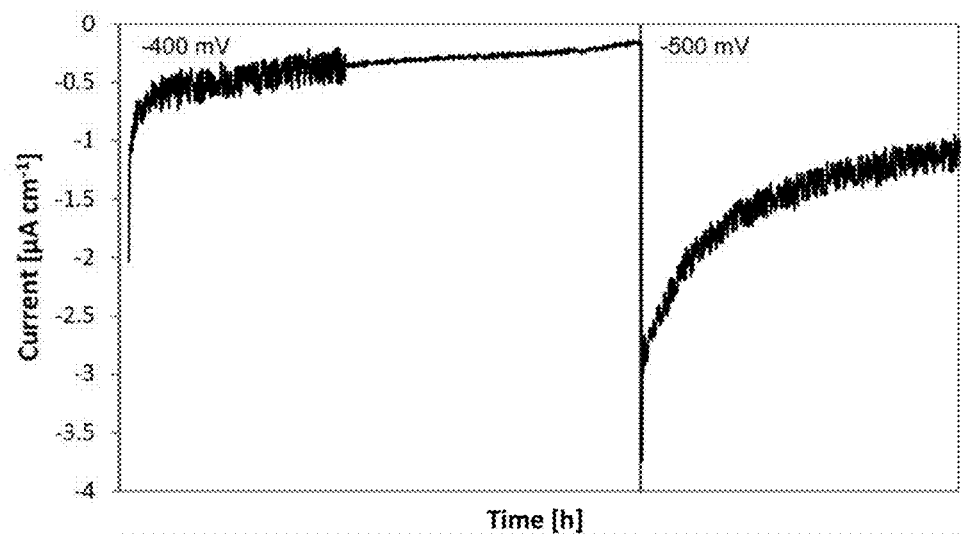
Figure 10B:
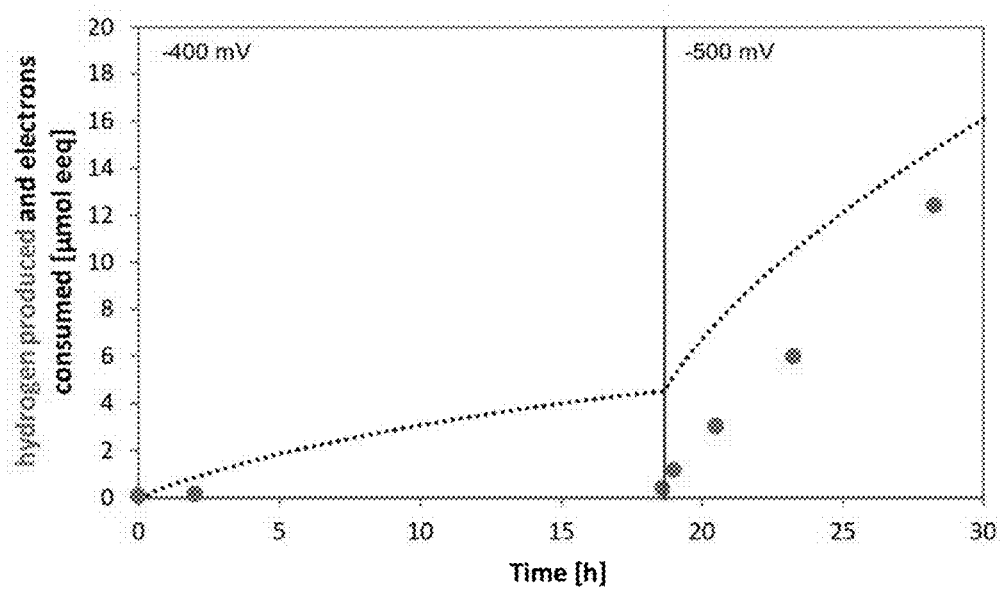

FIGS. 10A and 10B show the performance of a platinum foil electrode under the same conditions and in the same medium used for the IS4 biocathode. FIG. 10A shows the current profile. FIG. 10B shows hydrogen accumulation (gray circles) and electrons consumed (dotted line). Current and hydrogen accumulation are very low at −400 mV versus SHE, and the coulombic efficiency of hydrogen evolution is below 10%. At −500 mV, current consumption and hydrogen evolution rates increased by one order of magnitude and the coulombic efficiency of hydrogen evolution increased to 85%.

Figure 11A:
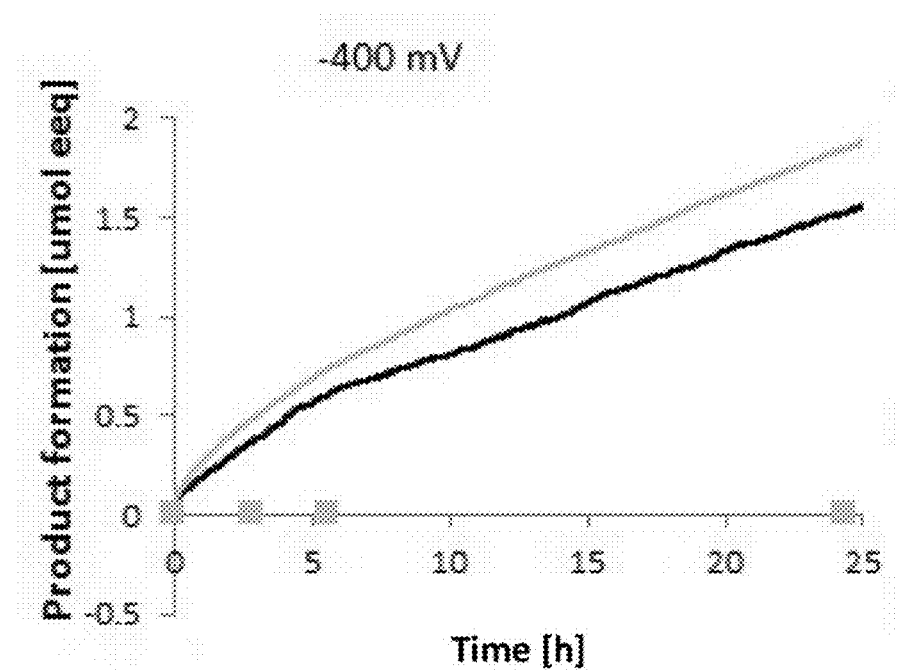
Figure 11B:
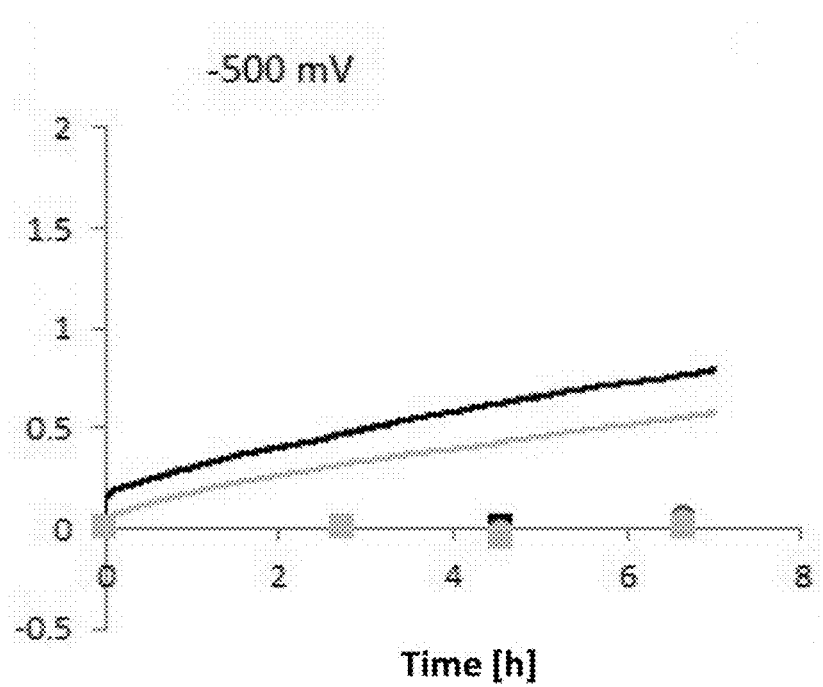
Figure 11C:
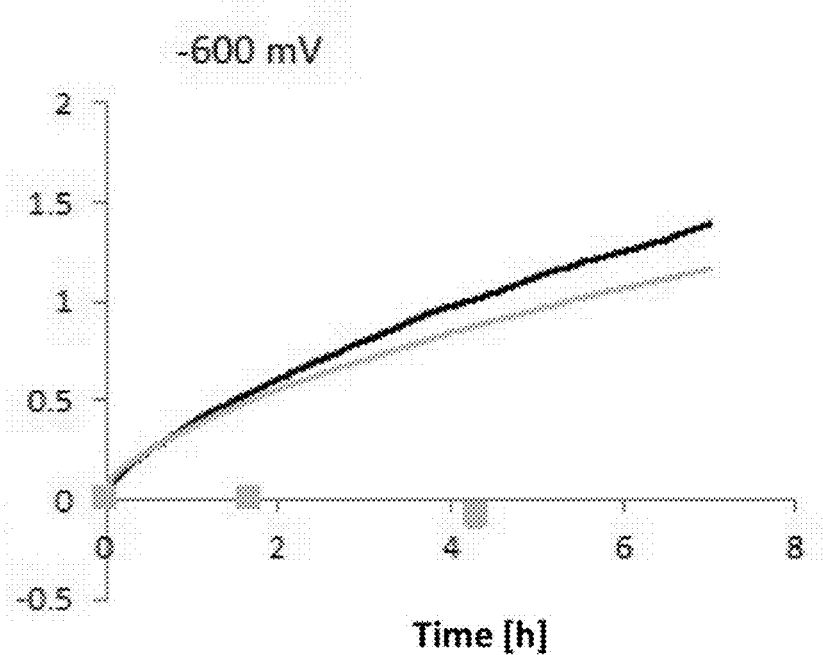

FIGS. 11A-11C show background reaction rates with uninoculated controls or *M. maripaludis* pure culture. Hydrogen and methane formation as well as current consumption by uninoculated controls (black) and *M. maripaludis* (grey) at −400 mV (FIG. 11A), −500 mV (FIG. 11B), and −600 mV (FIG. 11C) versus SHE. No significant accumulation of hydrogen or methane was observed. All values are shown in μmol electron equivalents to facilitate comparison. Note the different scales in FIGS. 11A-11C.

DETAILED DESCRIPTION

The practice of the present invention will employ, unless otherwise indicated, conventional methods of chemistry, biology, biochemistry, and molecular biology and recombinant DNA techniques within the skill of the art. Such techniques are explained fully in the literature. See, e.g., *Microbial Electrochemical and Fuel Cells: Fundamentals and Applications* (K. Scott and E. H. Yu eds., Woodhead Publishing, 2015); *Organic Electrochemistry* (O. Hammerich and B. Speiser eds., CRC Press, 5$^{th}$ edition, 2015); A. L. Lehninger, Biochemistry (Worth Publishers, Inc., current addition); and Sambrook et al., *Molecular Cloning: A Laboratory Manual* (3$^{rd}$ Edition, 2001).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "an electron" includes two or more electrons, and the like.

The term "about," particularly in reference to a given quantity, is meant to encompass deviations of plus or minus five percent.

"Biocompatible" refers to a material that is non-toxic to a cell or microorganism.

"Interspecies electron transfer" refers to transfer of reducing equivalents between different species of microorganisms.

The phrase "microbial electrosynthesis" as used herein refers to the production of organic compounds by a process in which electrons from a cathode are used for microbial reduction of protons to produce $H_2$ or carbon dioxide to produce formate. Subsequent microbial consumption of the $H_2$ or formate together with $CO_2$ results in biosynthesis of organic compounds.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that microbial electrosynthesis can be accomplished using co-cultures coupling cathodic electron uptake with biosynthesis reactions via interspecies hydrogen transfer. In particular, the inventors have shown that the Fe(0)-corroding sulfate-reducing bacterium, *Desulfopila corrodens* strain IS4, can catalyze an electron uptake reaction from a cathode to form molecular hydrogen as an intermediate. Electron uptake and hydrogen evolution rates were an order of magnitude higher in the presence of the bacterium than rates obtained with an abiotic platinum cathode. The inventors have further shown that hydrogenotrophic strains, such as *Methanococcus maripaludis* and *Acetobacterium woodii* can utilize the hydrogen so produced for biosynthesis of methane and acetate, respectively, in co-cultures with *Desulfopila corrodens* strain IS4 (see Example 1).

In order to further an understanding of the invention, a more detailed discussion is provided below regarding microbial electrosynthesis with co-cultures of hydrogen producing microorganisms and hydrogenotrophic microorganisms for production of desired organic compounds.

A microbial electrosynthesis system comprises a cathode, an anode, and a power supply electrically connected to the cathode and the anode. A first microorganism is cultured on or attached to the cathode, wherein the first microorganism is capable of accepting electrons from the cathode resulting in either reduction of protons to produce hydrogen or reduction of carbon dioxide to produce formate. A second microorganism is cultured in sufficient proximity to the first microorganism to allow consumption of the hydrogen or the formate generated by the first microorganism, wherein the second microorganism is capable of biosynthesis of an organic compound of interest from carbon dioxide and the hydrogen or the formate generated by the first microorganism. In certain embodiments, the first microorganism or the second microorganism is a bacterium or an archaeon Media suitable for microbial growth or metabolic activity is supplied to the first microorganism and the second microorganism in the microbial electrosynthesis system.

The electrodes in the microbial electrosynthesis system may be formed of an electrically conductive material, such as a conductive carbon material or a metal, metal oxide, or metal alloy, and are preferably biocompatible with cells that contact the electrodes. For example, the electrodes may comprise any one or more of graphite or other conductive carbon material, indium tin oxide (ITO), fluorine-doped tin oxide (FTO), platinum, titanium, silver, or gold, or a metal alloy or an oxide comprising at least one of tin, platinum, titanium, silver, or gold.

In certain embodiments, the microbial electrosynthesis system further comprises one or more chambers. For example, the second microorganism may be contained inside a chamber. The anode and the cathode may be contained inside the same chamber, or the microbial electrosynthesis system may comprise a first chamber comprising the cathode and a second chamber comprising the anode, wherein the first microorganism and the second microorganism are inside the first chamber comprising the cathode. The chambers are preferably composed of a transparent material (e.g., plastic or glass) to allow visualization of the cell cultures of the microorganisms.

In certain embodiments, at least one membrane is used to separate one or more chambers. For example, the microbial electrosynthesis system may comprise a membrane separating a cathode chamber and an anode chamber. The membrane may allow, for example, proton exchange (e.g., Nafion membrane), cation exchange, or anion exchange between the first chamber and the second chamber. In another embodiment, the membrane is a bipolar membrane (i.e., the membrane generates from the medium protons on the cathode facing side and anions on the anode facing side). Membranes suitable for electrosynthesis are commercially available, for example, from Fuel Cell Store (College Station, Tex.), Sigma-Aldrich (St. Louis, Mo.), Perma Pure LLC (Lakewood, N.J.), and DuPont (Wilmington, Del.).

A culture of a hydrogen-producing microorganism or formate-producing microorganism is grown on the surface of the cathode ("microbial biocathode") to allow microbial uptake of electrons from the cathode. Electron transfer from the cathode to the microorganism results in reduction of protons to produce hydrogen or reduction of carbon dioxide to produce formate, respectively. In order to utilize the hydrogen gas or formate, a culture of a second microorganism is grown in sufficient proximity to the microbial biocathode to allow consumption of the hydrogen or formate. For example, the second microorganism can be grown inside the cathode chamber. Carbon dioxide together with the hydrogen or formate is metabolized by the second microorganism resulting in production of organic compounds.

The hydrogen or formate producing microorganism may be any strain of bacteria or archaea capable of accepting electrons from an electrode to generate $H_2$ or formate. Exemplary hydrogen or formate producing microorganisms include *Desulfopila* (e.g., *Desulfopila corrodens*), *Geobacter* (e.g., *Geobacter sulfurreducens*, *Geobacter metallireducens*), and *Desulfovibrio* (e.g., *Desulfovibrio* sp.) species. Production of $H_2$ from the microbial biocathode depends on the ability of the microorganism to catalyze proton reduction using the electrode as a direct electron donor, which generally relies on a microbial hydrogenase. Microorganisms having a formate dehydrogenase or a formate-hydrogen lyase may also be able to generate formate from reduction of carbon dioxide.

Microbial electrosynthesis of organic compounds results from subsequent interspecies electron transfer through the consumption of the $H_2$ or formate by another microorganism. The second microorganism is chosen for its ability to synthesize a particular organic product of interest from the $CO_2$ and $H_2$ or formate.

In one embodiment, a methanogen is used to produce organic compounds. Many methanogens can use either $H_2$ or formate as a source of electrons for reduction of $CO_2$ to methane. Hydrogenotrophic methanogens produce energy from the biosynthesis of methane according to the chemical equation: $4\ H_2$ (gas)$+CO_2$ (gas)$\rightarrow CH_4$ (gas)$+2\ H_2O$. Methanogens that can be used in the practice of the invention include, but are not limited to, archaea methanogens belonging to the phylum Euryarchaeota, including the six orders Methanobacteriales, Methanocellales, Methanococcales, Methanomicrobiales, Methanosarcinales, and Methanopyrales. Exemplary methanogens include *Methanococcus maripaludis*, *Methanocaldococcus jannaschii*, *Methanobrevibacter ruminantium*, *Methanothermobacter thermautotrophicus*, *Methanopyrus kandleri*, *Methanosphaera stadtmanae*, *Methanobrevibacter smithii*, *Methanocella paludicola*, *Methanocella* sp., *Methanocaldococcus fervens*, *Methanocaldococcus infernus*, *Methanocaldococcus vulcanis*, *Methanococcus aeolicus*, *Methanococcus vannielii*, *Methanococcus voltae*, *Methanocorpusculum labreanum*, *Methanoculleus marisnigri*, *Methanosphaerula palustris*, and *Methanospirillum hungatei*.

In another embodiment, an acetogen is used to produce organic compounds. Hydrogenotrophic acetogens, produce energy from the biosynthesis of acetate according to the chemical equation: $4\ H_2$ (gas)$+2\ CO_2$ (gas)$\rightarrow CH_3COO^-+H^-+2\ H_2O$. Acetogens that can be used in the practice of the invention include, but are not limited to, the *Acetobacterium* genus of anaerobic, gram-positive bacteria belonging to the Eubacteriaceae family, such as *Acetobacterium woodii*, *Acetobacterium bakii*, *Acetobacterium carbinolicum*, *Acetobacterium dehalogenans*, *Acetobacterium fimetarium*, *Acetobacterium malicum*, *Acetobacterium paludosum*, *Acetobacterium psammolithicum*, *Acetobacterium submarinus*, *Acetobacterium tundrae*, *Acetobacterium wieringae*, and *Acetobacterium* sp.; acetogenic thermophilic bacteria of the Thermoanaerobacteraceae family, including members of the genus *Moorella*, such as *Moorella thermoacetica*, the genus *Thermoanaerobacter*, such as *Thermoanaerobacter kivui*, and the genus *Thermacetogenium*, such as *Thermacetogenium phaeum*; and members of the *Clostridium* genus of anaerobic gram-positive bacteria, such as *Clostridium ljungdahlii* and *Clostridium autoethanogenum*. Acetogens also include acetogenic archaea of the phylum Bathyarchaeota.

Many methanogens and acetogens can use either $H_2$ or formate as a source of electrons for biosynthesis. Generally, such microorganisms have a formate dehydrogenase to allow formate to be utilized as an electron donor. Some hydrogenotrophic methanogens and acetogens only use $H_2$ as an electron donor for the reduction of $CO_2$.

Media suitable for growth of the two microorganisms is added to the cathode chamber. For example, the growth media for the microorganism uptaking cathodic electrons may comprise an electron acceptor (e.g., sulfate for a sulfate-reducing microorganism, nitrate for a nitrate-reducing microorganism, or fumarate for a fumarate-reducing microorganism). Carbon dioxide may be supplied to promote biosynthesis of organic compounds by a methanogen, acetogen, or other microorganism capable of synthesizing desired organic compounds. Microorganisms can be cultured, for example, in a basal medium containing the minimal requirements for growth including trace minerals, phosphate, and iron, but may benefit from a complex medium containing additional nutrients, such as casamino acids, vitamins, yeast extract, and acetate to enhance growth. Media may be supplied manually or automatically with a continuous, batch, or semi-batch fed culture system. The supply of media may be controlled to limit the cell density of the hydrogen or formate producing microorganism on the cathode to optimize efficiency and reduce costs. In one embodiment, the media supply is adjusted to control biomass such that the cell density of the hydrogen or formate producing microorganism is maintained between about $10^7$ to about $10^8$ cells $cm^{-2}$ on the cathode surface. In certain embodiments, one or more of the microorganisms used in microbial electrosynthesis are obligate anaerobes, in which case, care should be taken to eliminate oxygen from the culture environment.

The synthesis capabilities of methanogenic and acetogenic microorganisms are not limited to methane and acetic acid, but can also include compounds derived therefrom for which biochemical biosynthetic pathways exist. For example, acetyl coenzyme A (acetyl-CoA), derived from $CO_2$, is an intermediate in the Wood-Ljungdhal pathway used by methanogens and acetogens to fix $CO_2$ and naturally used in a number of biosynthetic pathways to produce various organic compounds, including formate, acetic acid, butyric acid, ethanol, isopropanol, butanol, 1,3-propanediol, 2,3-butanediol, and acetone. Additionally, microorganisms can be engineered with new synthetic pathways to produce other desired compounds.

A microbial electrosynthesis system or agents for performing microbial electrosynthesis, as described herein, may be included in a kit. The kit may comprise one or more containers holding a microbial electrosynthesis reactor and/or one or more microorganisms, such as a microorganism capable of cathodic electron uptake (e.g., hydrogen-producing microorganism or formate-producing microorganism), a microorganism capable of biosynthesis of a compound of interest by reduction of carbon dioxide via interspecies electron transfer (e.g., methanogen, acetogen, or other microorganism capable of synthesizing desired organic compounds), and media suitable for their growth. Suitable containers for the compositions include, for example, bottles, vials, syringes, and test tubes. Containers can be formed from a variety of materials, including glass or plastic. A container may have a sterile access port (for example, the container may be a vial having a stopper pierceable by a hypodermic injection needle). Additionally, instructions (e.g., written, CD-ROM, DVD, Blu-ray, digital download, etc.) for performing microbial electrosynthesis may be included with the kit.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Enhanced Microbial Electrosynthesis by Using Defined Co-Cultures

Introduction

In the present study, we investigated the Fe(0)-corroding sulfate-reducing strain IS4 as a biocatalyst to enhance the electron uptake rate in a bioelectrosynthesis system. Strain IS4 was previously shown to form molecular hydrogen transiently during cultivation on Fe(0) (Dinh et al. (2004) Nature 427:829-832). To provide the proof of concept that the overall rates of electrosynthesis can be increased by co-cultivation of a specialized electron-uptaking strain with another microbe capable of producing a desired product, we constructed and examined electron flow in defined co-cultures of strain IS4 with the methanogen *M. maripaludis* and the acetogen *Acetobacterium woodii*. Our data demonstrate the importance of interspecies hydrogen transfer in cathode-associated microbial communities and highlights a primary role of electron uptake strains as ecosystem engineers in these communities.

Materials and Methods

Microbial Strains and Cultivation

Strain IS4 (DSM 15630) and *A. woodii* (DSM 1030) were obtained from the German Collection of Microorganisms and Cell Cultures. The *M. maripaludis* strain MM901 was obtained from the laboratory of Dr. John Leigh, U W (Costa et al. (2013) MBio 4:e00062-00013). Strain IS4 was routinely cultivated in artificial seawater medium containing 28 mM sodium sulfate as electron acceptor (Dinh et al., supra). *A. woodii* was initially cultivated in a modified DSMZ medium 311. *M. maripaludis* was routinely cultured in a modified DSMZ medium 141.

For co-cultivation, *A. woodii* and *M. maripaludis* were transferred to artificial seawater medium (amended with 0.1% yeast extract in case of *A. woodii*) and transferred at least twice in this medium before the co-culture experiment.

All cultures were maintained in butyl-rubber stopper sealed 120 ml or 160 ml serum vials containing 50 ml of medium with a headspace of 80% $H_2$ and 20% $CO_2$ as electron donor and sole carbon source, respectively.

Electrochemical Experiments

Electrochemical reactors were setup as described previously (Lohner et al. (2014) ISME J 8:1673-1681). The electrochemical cell consisted of a two chambered, gas-tight borosilicate H-cell, in which anode and cathode chambers (150 ml each) were separated by a Nafion 117 proton-exchange membrane as described previously (Lohner et al., supra). The medium exposed area of the graphite electrodes (conductive graphite bars ¼×¼ inch, McMaster-Carr) was 8 $cm^2$, and this area was used to calculate specific electron transfer and product formation rates. The reference electrodes used were Ag/AgCl electrodes (model RE-5B, BASi, West Lafayette, Ind., USA) in 3 M NaCl. Autoclaved reactors were flushed with a sterile mix of 80% $N_2$ and 20% $CO_2$ until oxygen was completely flushed out, the reference electrode was inserted and 90 ml sulfate-free artificial seawater medium was anoxically and aseptically transferred into the anode and cathode compartments with a $N_2/CO_2$ flushed plastic syringe while continuously flushing the reactor. Reactors were disconnected from the gas stream and maintained at 30° C. A volume of 3-6 ml of early stationary phase culture of the indicated organisms was added to the cathode compartment, resulting in an initial gas phase volume of 43-46 ml. The change in gas to liquid ratio due to sampling was considered when calculating absolute amounts of different substances in the reactor. In all, 250 μM sulfate was added to reactors containing strain IS4. The cathode was poised at the indicated potentials after inoculation. Electric current and product formation were followed over time. Cyclic voltammograms were recorded after a steady current or product formation rate had established, that is, after the establishment of the IS4 biocathode shown in FIG. 1 and the subsequent cultivation time needed to establish a stable co-culture with *M. maripaludis* in a subset of the reactors and after rate measurements shown in FIG. 3 (total of 312 hours cultivation time). The gas phase of all reactors was flushed with $N_2/CO_2$ at the time of introducing a second organism. Platinum foil (17.5 cm² immersed surface) was used as cathode in the same setup to obtain hydrogen evolution rates for a model inorganic catalyst under identical conditions.

Analytical Procedures

Methane and high concentrations of hydrogen were determined using a gas chromatograph with nitrogen as the carrier gas (equipped with both a thermal conductivity detector and a flame ionization detection detector). Low concentrations of $H_2$ were determined using a reductive trace gas analyzer, and soluble compounds such as formate and acetate were determined using high-performance liquid chromatography as described previously (Lohner et al., supra). To allow for a better comparison of formation rates of different products and electron flux, concentrations were converted to concentrations in electron equivalents (for example, μmol eeq) where appropriate. Concentrations in μmol eeq were calculated by multiplying the concentration of a given compound by the number of electrons required for its formation from $CO_2$.

Electron Microscopy

Samples were fixed in 4% paraformaldehyde with 2% glutaraldehyde in 0.1 M sodium cacodylate buffer (pH 7.4) for 24-48 hours at 4° C., rinsed in the same buffer and post-fixed in 1% aqueous $OsO_4$ for 2 hours before dehydration in an increasing ethanol series (50-70-90-100%, 15 minutes each). Samples were then critical point dried (Tousimis 815B, Rockville, Md., USA) with liquid $CO_2$, mounted on aluminum pin stubs and sputter-coated with Au/Pd using a Denton Desk II sputter-coater (Denton Vacuum, Moorestown, N.J., USA) before visualizing with a Zeiss Sigma FESEM (Carl Zeiss Microscopy, Thorn-wood, N.Y., USA) using InLens secondary electron detection at 2-3 kV. At least three different positions encompassing at least 5000 μm² electrode surface have been analyzed to estimate cell counts on the electrode surface.

Complete Description of Growth Media

Strain IS4 was routinely cultivated in artificial seawater medium (ASW) containing 28 mM sodium sulfate as electron acceptor (Dinh et al., supra). The ASW contained per liter: 20 g NaCl, 3 g $MgSO_4$.7 $H_2O$, 0.25 g $NH_4Cl$, 0.5 g KCl, 0.15 g $CaCl_2$.2 $H_2O$, 1 ml trace element solution SL-10, 1 ml selenite-tungstate solution, 150 Na—K—$PO_4$ buffer, 1 mM $Na_2S$ and 1 ml Vitamin solution and 30 mM $NaHCO_3$. *Acetobacterium woodii* was initially cultivated in a modified DSMZ medium 311 containing per liter: 0.50 g $NH_4Cl$, 0.50 g $MgSO_4$.7 $H_2O$, 0.25 g $CaCl_2$.2 $H_2O$, 2.25 g NaCl, 2 mg $FeSO_4$.7$H_2O$, 0.1% yeast extract, 1 ml trace element solution SL-10, 1 ml selenite-tungstate solution, 150 μM Na—K—$PO_4$ buffer, 1 mM $Na_2S$ and 1 ml Vitamin solution and 30 mM $NaHCO_3$. *Methanococcus maripaludis* was routinely cultured in a modified DSMZ mineral medium 141 containing 0.34 g KCl, 4 g $MgCl_2$.6 $H_2O$, 3.45 g $MgSO_4$.7 $H_2O$, 0.25 g $NH_4Cl$, 0.14 g $CaCl_2$×2 $H_2O$, 18 g NaCl, 2 mg $Fe(NH_4)_2$ $(SO_4)_2$, 1 ml trace element solution SL-10 (Widdel et al. 1983), 1 ml selenite-tungstate solution (4 mg $Na_2Wo_4$. 2 $H_2O$, 3 mg $Na_2SeO_3$.5 $H_2O$ in 1 L), 150 μM Na—K—$PO_4$ buffer, 1 mM $Na_2S$ and 1 ml Vitamin solution (from DSM medium 141) and 30 mM $NaHCO_3$. Phosphate, sulfide, bicarbonate and vitamins were added after autoclaving in all media. The pH was adjusted to 7.0 in all media.

Effect of Measurement Uncertainties in the Electrochemical Setup on the Equilibrium Potential Calculations We assume the potentials of the Ag/AgCl reference electrodes are accurate to a level of ±5 mV. Drift in the reference electrode potentials (caused e.g. by slow sulfide poisoning of the electrode) was corrected for during analysis by measuring the electrode potential before mayor potential sensitive manipulations of the system (e.g. measuring CVs or close to steady state hydrogen partial pressures) by inserting an additional self-made Ag/AgCl electrode in the reactors and recording the difference in potentials. The self-made reference electrode consisted of a AgCl coated silver wire in 3 M NaCl saturated with AgCl in a plastic 1 ml syringe housing. The ion bridge was a 18 G×1.5 in needle filled with a 3 NaCl and 1.5% agarose gel. This needle electrode was inserted into the electrochemical reactors through the rubber stopper next to the regular reference electrode. Due to the high resistance of this ion bridge, this reference electrode needed several minutes of equilibration, before the potential could be recorded. The pH of the catholyte solution was measurable at an accuracy of ±0.1 pH unit. However, the local pH at the cathode surface is likely higher due to the local consumption of protons for $H_2$ production or electrosynthesis. In addition, $CO_2$ was removed from the solution over time due to cell growth and a shift the pH to slightly more alkaline conditions. Within these limits, the theoretically achievable hydrogen partial pressure at a cathode potential of −400 mV (±5 mV) and a pH of 7.0 (±0.1) could vary within almost one order of magnitude and ranged between 0.09 and 0.47 bar based on thermodynamic calculations.

These calculations were performed using the Nernst equation $$E = E° + \frac{RT}{zF}\ln\frac{Cred}{Cox},$$

[where E is the equilibrium potential of the reaction, $E°'$ is the standard equilibrium potential at a temperature of 298 K, R is the universal gas constant (R=8.31 J K⁻¹ mol⁻¹), T is the temperature in Kelvin, F is the Faraday constant (F=9.64·10⁴ C mol⁻¹), z is the number of moles of electrons transferred in the reaction, and $c_{ox}$ and $c_{red}$ are the concentrations of the reduced and oxidized compounds ($H_2$ and $H^+$, respectively)]. By varying E between −395 and −405 mV and c($H^+$) between $10^{-6.9}$ and $10^{-7.1}$ (corresponding to pH=6.9 and 7.1) Theoretical $H_2$ partial pressures of between 0.09 and 0.47 bar were calculated. Thus, at a potential at −395 mV and a pH of 7.1, the maximum hydrogen concentration that could be achieved based on thermodynamic constraints is 0.09 bar. This is very close to the maximum hydrogen partial pressure observed in our experiments (see FIGS. 1B and 8).

Results

Establishment of an Active Strain IS4 Biocathode

Figure 1A:
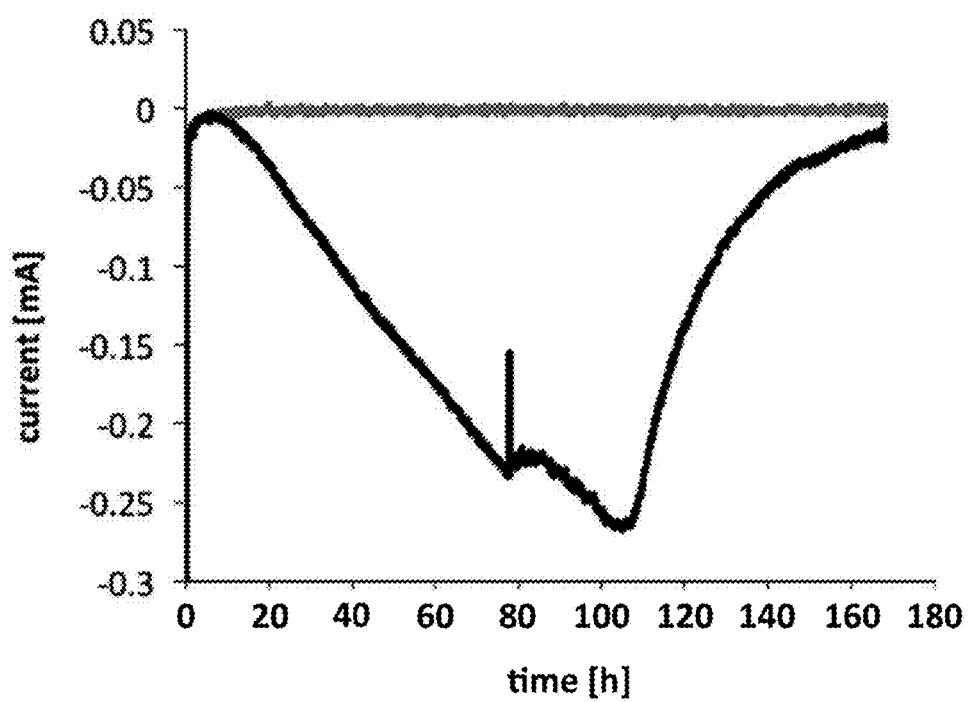
FIG. 1A-1C show a startup of a bioreactor with strain IS4 as a biocathode. Strain IS4 was inoculated into a bioelectrochemical reactor with a cathode potential of −400 mV versus standard hydrogen electrode and compared with an un-inoculated control.
Figure 1B:
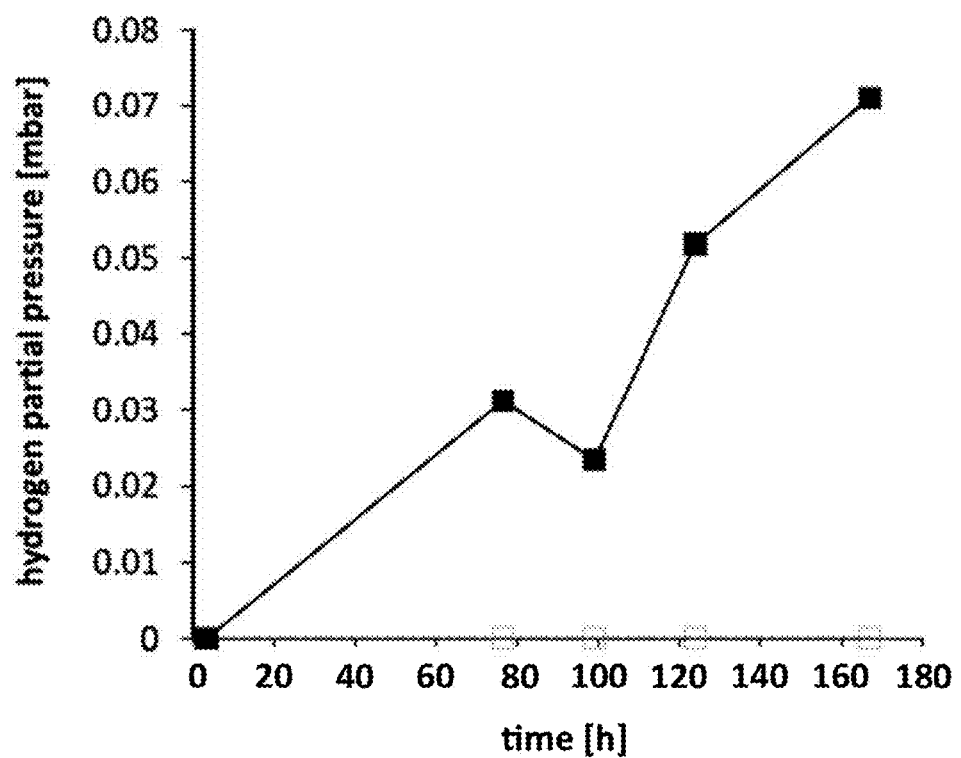
Figure 1C:
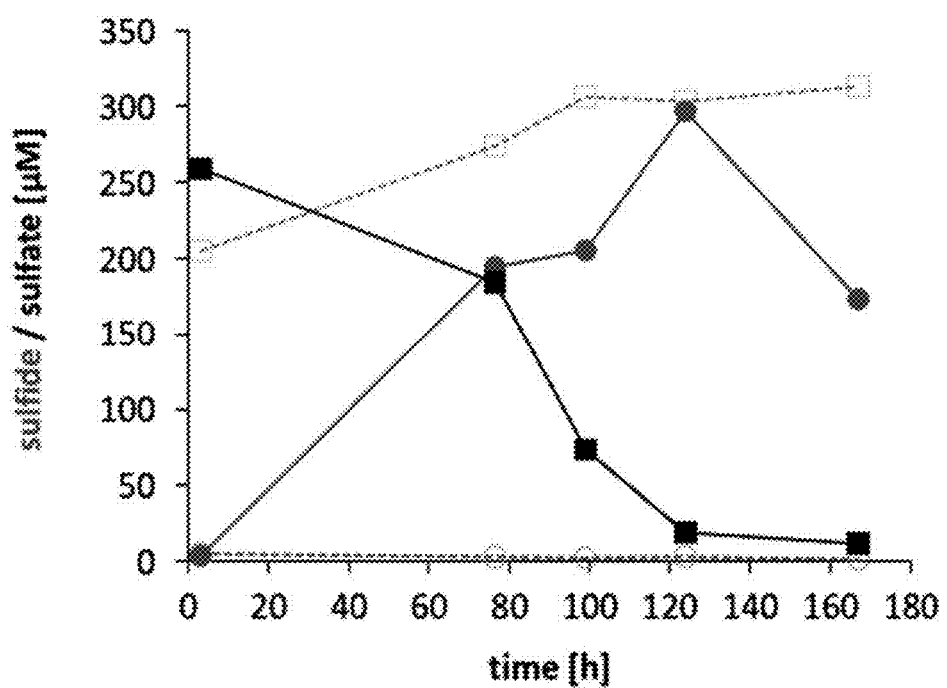
Figure 6:
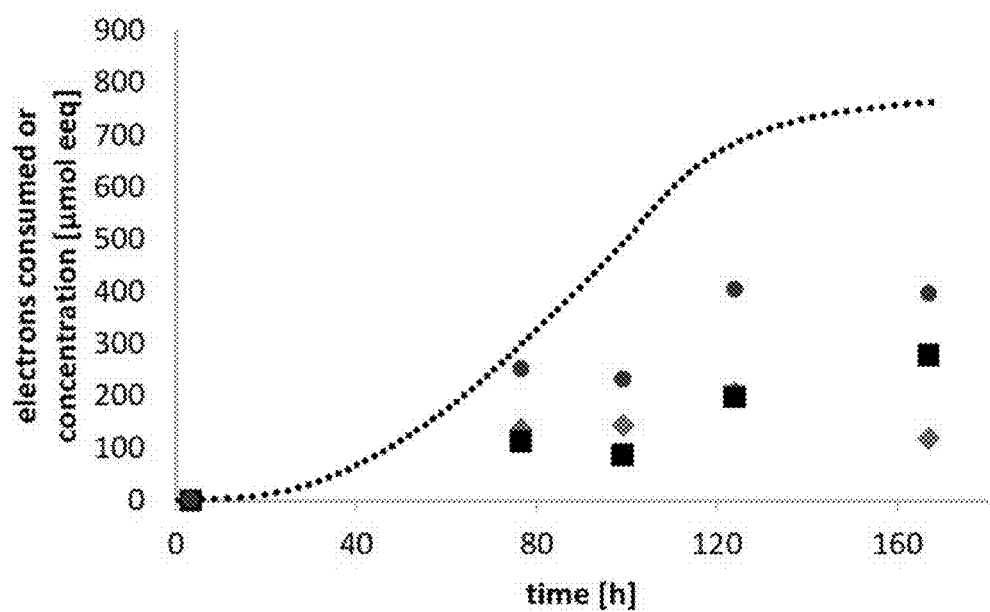
FIG. 6 shows coulombic efficiencies during the establishment phase of the biocathode as shown in FIG. 1. Current consumption (dotted line) as well as electrons consumed for the formation of sulfide (red diamonds), the formation of $H_2$ (black squares), and total electrons consumed for both processes (blue circles) are shown.
Figure 7A:
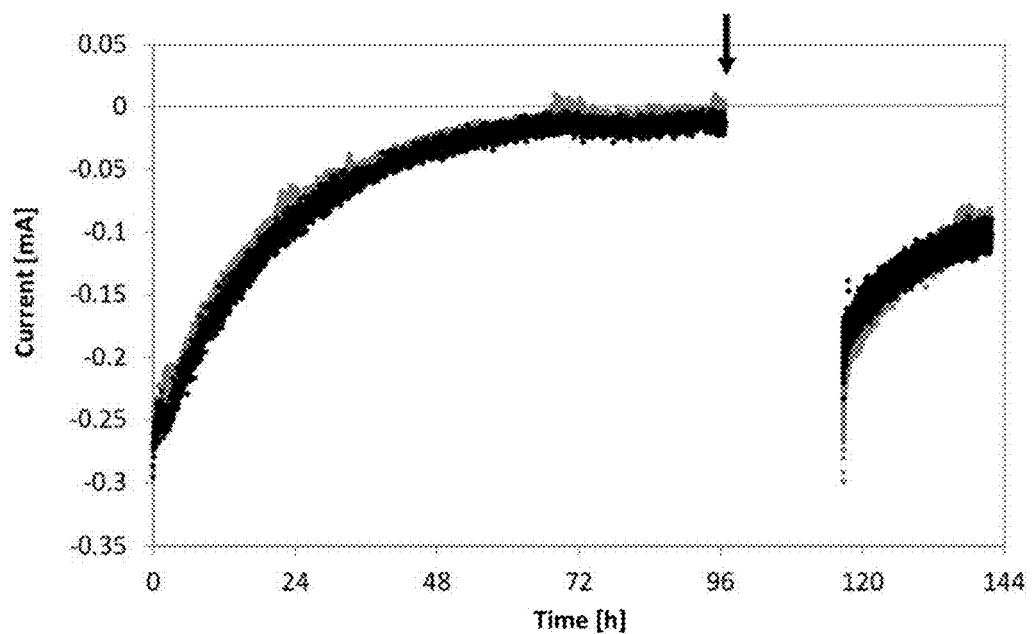
FIGS. 7A and 7B show current consumption (FIG. 7A) and hydrogen accumulation (FIG. 7B) in two reactors with an active strain IS4 biocathode. Strain IS4 was established at the cathode by addition of 0.25 mM sulfate to the medium according to FIG. 1. After sulfate was consumed, the reactors were flushed thoroughly with $N_2/CO_2$ (80/20). The reactors were then reconnected to the potentiostat and the cathode was poised at −400 mV vs. SHE. Hydrogen accumulated to 100-120 μmol/reactor (corresponding to 40-60 mbar $H_2$ partial pressure), which is close to the thermodynamic equilibrium potential achievable at −400 mV at circumneutral pH. Current consumption (FIG. 7A) and hydrogen accumulation (FIG. 7B) follow the same trend and current consumption declines as hydrogen accumulates to near-equilibrium concentrations. At the arrow, the reactors were flushed again with $N_2/CO_2$ (80/20) and incubated without current overnight to reach an equilibrium with the $H_2$ dissolved in the catholyte. When the electrode was poised to −400 mV again, current uptake and hydrogen evolution resumed, indicating that the decline in current consumption indeed resulted from the accumulation of $H_2$ in the bioelectrochemical reactors. The two colors and different symbols represent two independent replicates.
Figure 7B:
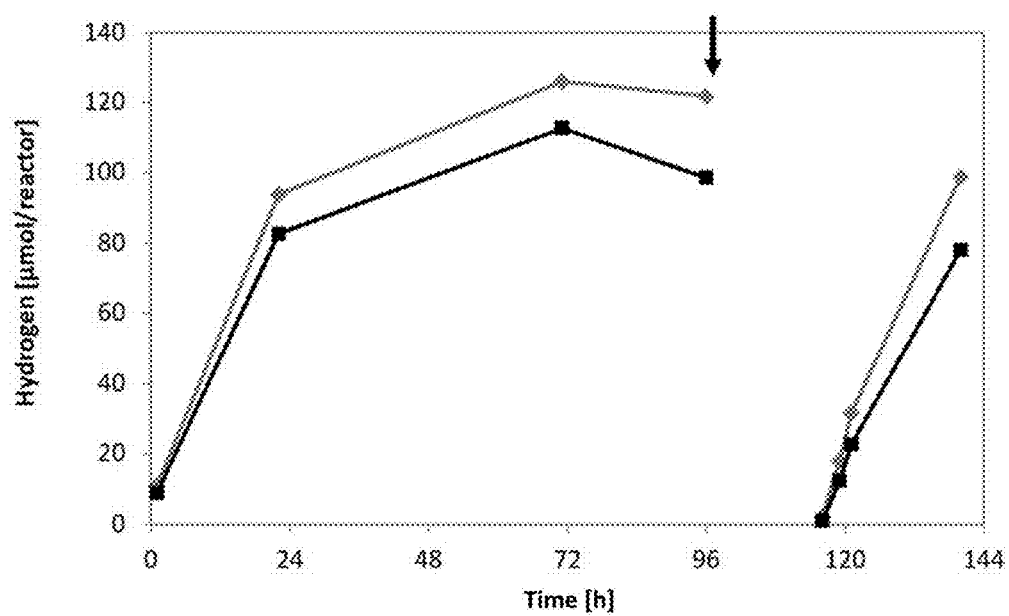

After inoculation of the biocathode in the presence of 250 μM sulfate, electron uptake in form of electrical current consumption by strain IS4 cells increased over time when the cathode was poised at −400 mV (versus standard hydrogen electrode) (see FIG. 1 for a representative experiment, FIG. 6 for coulombic efficiencies). No current consumption was observed using cell-free spent culture medium or without initial sulfate addition (data not shown), indicating that strain IS4 cells initially required sulfate as electron acceptor to establish a working biocathode. Current consumption increased for several days in the presence of sulfate before current consumption decreased sharply. Within this time period, sulfate concentration decreased and sulfide formed in equimolar concentrations as expected based on an active metabolism of this sulfate-reducing bacterium (FIG. 1C). The sharp decrease in current consumption coincided with sulfate depletion and hydrogen accumulation in the cathode compartment, indicating that strain IS4 cells utilized cathode-derived electrons for sulfate reduction. We also observed that electrochemical reactors containing cells of strain IS4 transiently accumulated molecular hydrogen even in the presence of sulfate (FIG. 1B). Notably, after sulfate depletion, rates of molecular hydrogen accumulation increased to ca. 0.2 pmol $h^{-1}$ $cm^{-2}$ relative to the initial rates of ca. 0.08 pmol $h^{-1}$ $cm^{-2}$ in the presence of sulfate. This indicates that upon depletion of sulfate electron uptake continued and electrons were used to reduce $H^+$ to form $H_2$, while sulfate reduction as $H_2$ (or electron) sink was blocked. Hydrogen accumulated to partial pressures of up to 0.08 bar at −400 mV versus standard hydrogen electrode. These partial pressures approached in our experimental setup the thermodynamic equilibrium concentration of the reaction $2H^+ + 2\ e^- \rightarrow H_2$, which prevented further consumption of cathodic electrons and explains the sharp decline of current consumption at −400 mV once sulfate was consumed (see FIG. 7).

Figure 2:
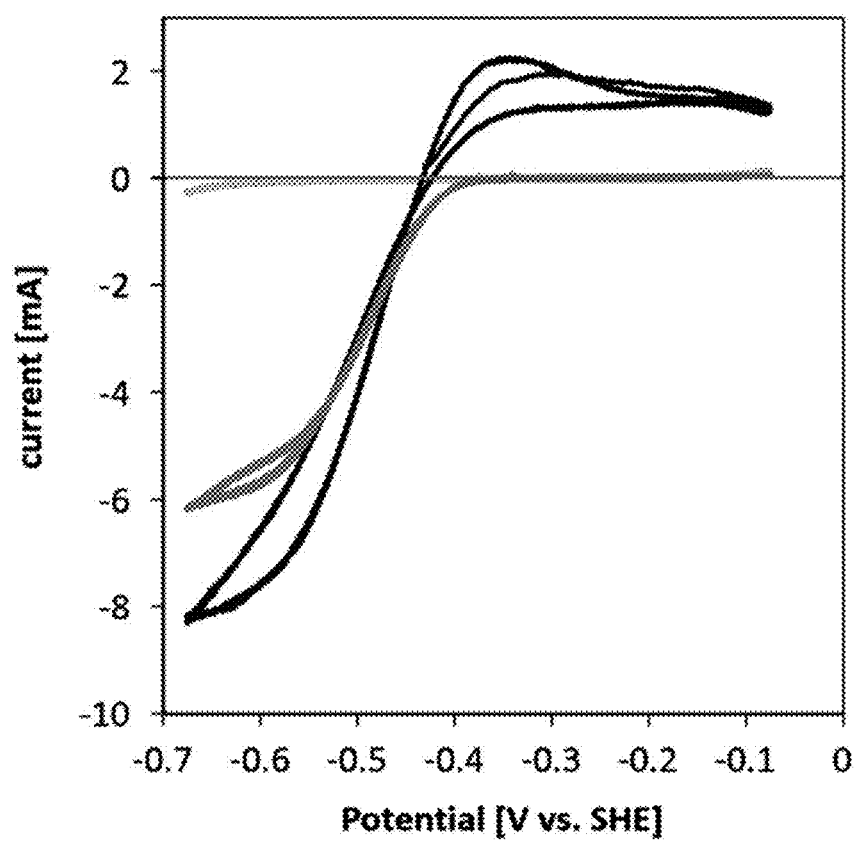
FIG. 2 shows cyclic voltammograms of graphite electrodes colonized by strain IS4 (black), strain IS4+M. maripaludis (medium gray) and pure M. maripaludis (light gray) after incubation at −400 mV versus standard hydrogen electrode. Scanning speed was 1 mV s$^{-1}$. For clarity one out of three replicates is shown. See FIG. 8 for CVs of all replicates.
Figure 8:
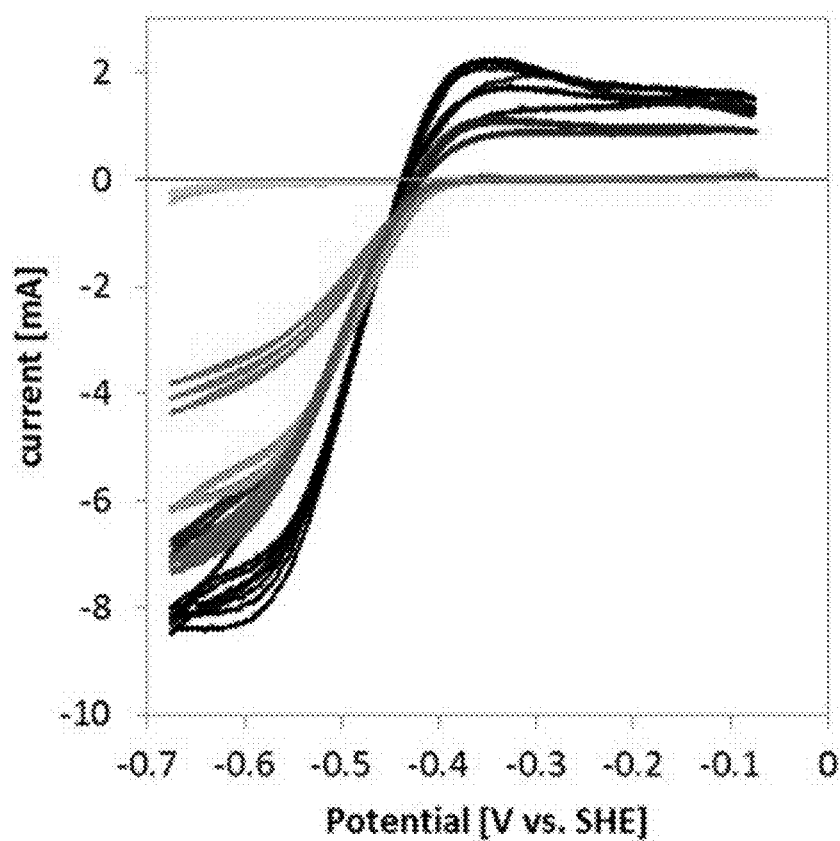
FIG. 8 shows cyclic voltammograms of graphite electrodes colonized by axenic strain IS4 (black), strain IS4+M.

The transient accumulation of $H_2$ raised the interesting possibility that $H_2$ formation at the cathode may be reversible in this bioelectrochemical system. If this were the case, we expected the formation of electric current from molecular hydrogen at a suitable electrode potential. Indeed, cyclic voltammetry revealed the typical wave pattern for reversible hydrogen evolution (FIGS. 2 and 8). This cyclic voltammetry (CV) profile also showed the absence of a noteworthy overpotential (<5 mV) for the hydrogen evolution reaction: the equilibrium potential of reversible hydrogen formation and hydrogen oxidation in our system was at about −425 mV under our experimental conditions, which is close to the calculated thermodynamic equilibrium potential of −421 mV at pH=7 and 30° C. At more positive potentials, current was produced indicating hydrogen oxidation, whereas at more negative potentials hydrogen was formed. Sulfide produced by strain IS4 during the incubation (<250 pM after flushing) did not result in a pronounced signal in the CVs and did not interfere with the catalytic wave of hydrogen production or oxidation (see FIG. 9).

Product Formation Rates at Different Electrode Potentials

Figure 3A:
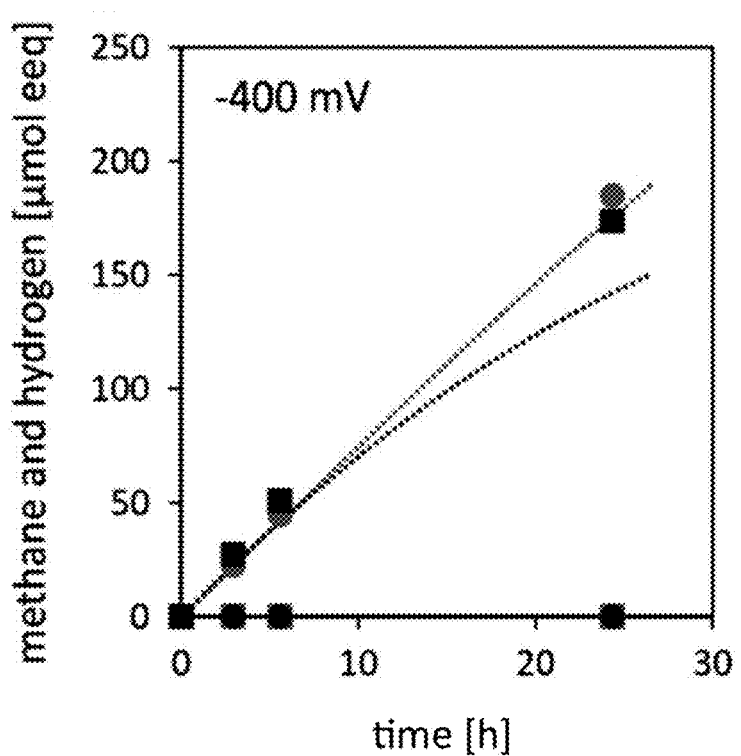
FIGS. 3A-3C show hydrogen and methane formation as well as current consumption by strain IS4 (black) and strain IS4 in co-culture with M. maripaludis (gray; red in online version) at different potentials. Methane (circles) and hydrogen (squares) are shown in pmol electron equivalents (pmol eeq) per reactor; current consumption (in pmol electrons consumed) by strain IS4 (black) or the co-culture (gray) is shown as dotted line. Note the different scales between (FIG. 3A) and (FIG. 3B) or (FIG. 3C).
Figure 3B:
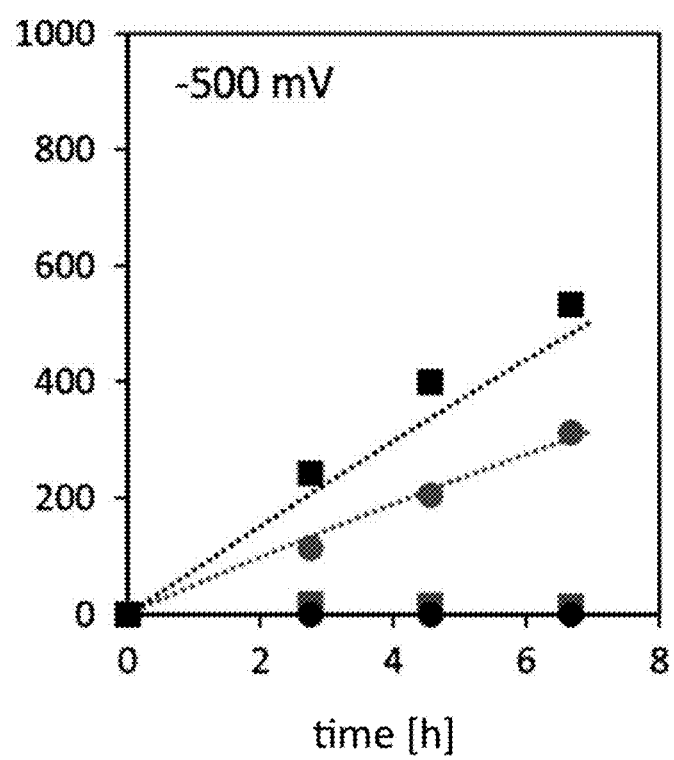
Figure 3C:
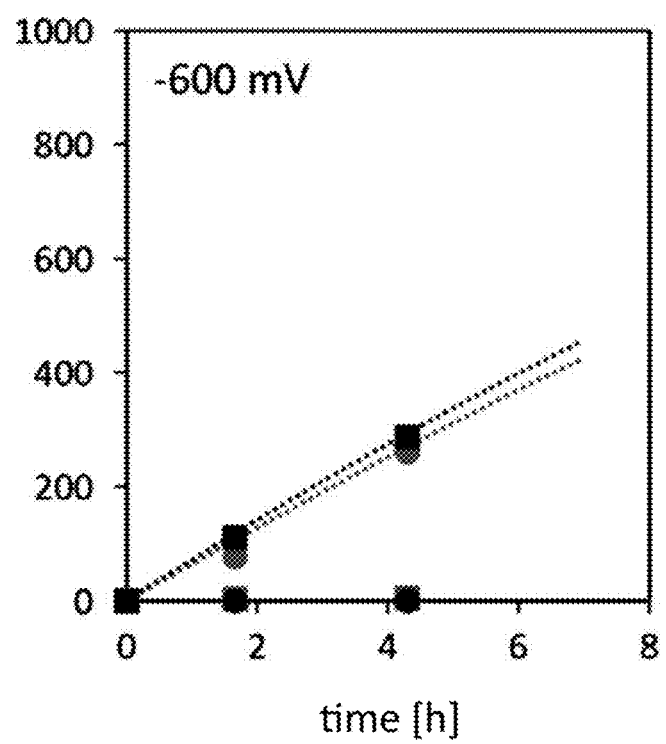
Figure 4A:
FIGS. 4A-4D show electron micrograph of plain graphite electrodes (FIGS. 4A and 4C) and graphite electrodes colonized with strain IS4 after incubation in electrochemical reactors (FIGS. 4B and 4D). Graphite electrodes were fixed after current consumption rates had reached a plateau that was stable for several days. Scale bars represent 10 μm (FIGS. 4A and 4B) and 1 μm (FIGS. 4C and 4D), respectively.
Figure 4B:
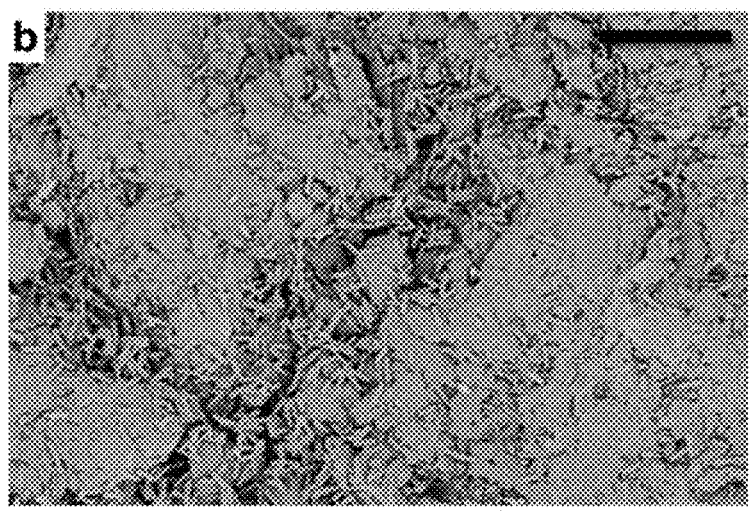
Figure 4C:
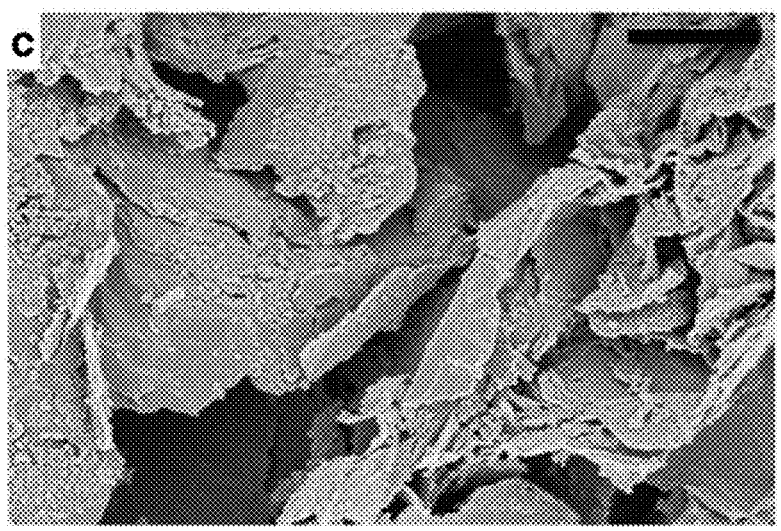
Figure 4D:
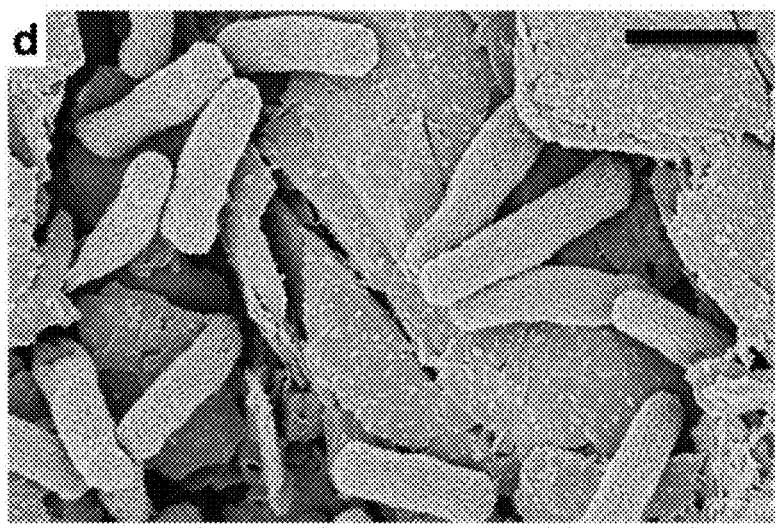

To investigate hydrogen formation by strain IS4 cells in greater detail, we performed experiments under sulfate-free conditions at different cathode potentials and followed hydrogen formation and current consumption over time. Before each experiment, all reactors containing previously established strain IS4 biocathodes were thoroughly flushed with $N_2/CO_2$ for 30 minutes to eliminate any residual hydrogen. Thereafter, hydrogen was formed at rates of 0.4-0.5 pmol $cm^{-2}$ $h^{-1}$ at a cathode potential of −400 mV (FIG. 3A). Hydrogen formation rates increased by one order of magnitude to 4-7 pmol $cm^{-2}$ $h^{-1}$ when the potential was lowered to −500 mV, but a further decrease in potential did not result in a significant change of hydrogen formation rate (FIGS. 3B and 3C). Under these conditions, strain IS4 formed hydrogen from cathodic electrons at a coulombic efficiency of 90-110% in all experiments. These hydrogen formation rates were more than one order of magnitude higher than hydrogen evolution rates obtained with platinum foil (0.002 pmol $cm^{-2}$ $h^{-1}$ at −400 mV and 0.14 pmol $cm^{-2}$ $h^{-1}$ at −500 mV, respectively (FIG. 10)) instead of the IS4 biocathode in an identical setup.

Electrosynthetic Formation of Methane by a Co-Culture of Strain IS4 and *M. Maripaludis*

To investigate whether the observed highly efficient hydrogen formation by strain IS4 cells can be coupled to the hydrogenotrophic production of carbon compounds from $CO_2$, we constructed a defined co-culture of strain IS4 with the methanogenic archaeon *M. maripaludis*. When *M. maripaludis* was added to a thoroughly $N_2/CO_2$-flushed, sulfate-depleted cathode chamber with an established strain IS4 biocathode, no accumulation of hydrogen but formation of methane was observed. Presumably, hydrogen was consumed rapidly to steady state concentrations of <500 p.p.m. in the gas phase due to methanogenesis. At −400 mV cathode potential this led to a small increase in current consumption (0.7-1.1 pmol electrons $cm^{-2}$ $h^{-1}$) compared with the reactors without methanogens (0.5-0.7 pmol electrons $cm^{-2}$ $h^{-1}$), most likely because the end product of the electron uptake step, hydrogen, was effectively scavenged by the methanogen (FIG. 3A). Lowering the cathode potential from −400 to −500 mV increased the rates of methane formation from 0.10-0.14 pmol cm-2 $h^{-1}$ to 0.6-0.9 pmol cm-2 $h^{-1}$ (FIG. 3B). This change in rate, however, was slightly lower than the change in the rate of hydrogen formation in the axenic IS4 culture (FIG. 3B). In agreement with those findings, a further decrease in potential to −600 mV did only result in a small increase in methanogenesis rate in the methanogenic co-culture (FIG. 3C). Notably, at cathode potentials of −400 mV and −600 mV, the rate of methane formation by the co-culture corresponded to the hydrogen formation rate by axenic strain IS4. No product formation was detected in un-inoculated controls or with an axenic *M. maripaludis* culture, and only marginal background current of 0.005-0.007 pmol electrons $cm^{-2}$ $h^{-1}$ was observed (FIG. 11). Collectively, these data show that a co-culture of strain IS4 and *M. maripaludis* efficiently converted cathodic electrons plus $CO_2$ into methane without the accumulation of intermediates.

Cyclic voltammetry measurements of the methanogenic co-culture indicated hydrogen formation was irreversible (FIG. 2). No current production was recorded in this co-culture at potentials more positive than the thermodynamic equilibrium potential for $H_2$ formation and oxidation. This confirmed that the methanogenic archaeon efficiently scavenged the molecular hydrogen formed at negative cathode potentials during the sweep and prevented hydrogen from reaching the electrode surface during hydrogen-oxidizing conditions. In addition, the onset potential of current consumption and presumably hydrogen formation shifted by >60 mV to more positive potentials, indicating a decrease in hydrogen partial pressure of more than two orders of magnitude. CVs of uninoculated reactors or reactors inoculated with axenic *M. maripaludis* (FIG. 2) only showed marginal catalytic currents.

Colonization of the Graphite Surface by Strain IS4

When the cathode chamber of an electrochemical H-cell was inoculated with strain IS4, electron microscopy revealed after 1 week of incubation (corresponding to a current consumption rate of 0.1 A $m^{-2}$ at this time) that cells on the electrode surface formed a patchy monolayer (FIG. 4). Cells were found clustered in 'cracks' and 'crevices' in the graphite surface, suggesting that cells might only be irregularly attached to the graphite surface. No pronounced production of visible extracellular polymeric substance was observed. A rough estimation of cell number on the electrode surface yielded cell densities of $10^7$-$10^8$ cells $cm^{-2}$ electrode surface. However, these cell counts and extrapolated values have to be treated with caution, because the graphite surface is very rough and cells can be buried below the visible surface of the electrode.

Formation of Acetate by a Co-Culture of Strain IS4 and *A. woodii*

Figure 5A:
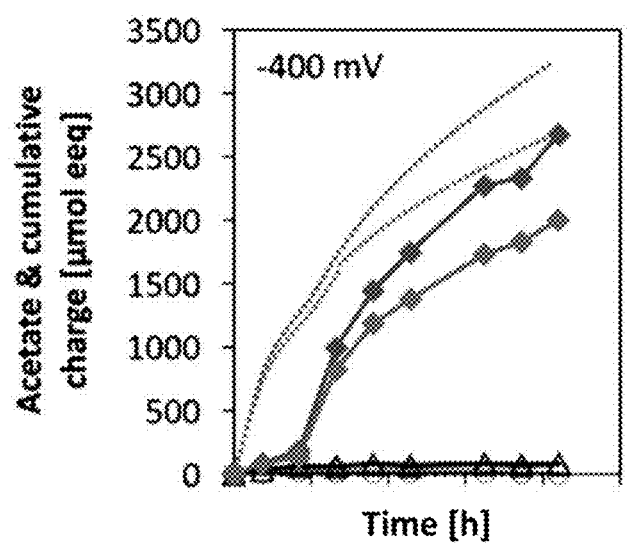
FIGS. 5A-5F show co-cultures of strain IS4 and A. woodii in the cathode compartment of electrochemical reactors. Acetate formation (filled symbols and solid lines) and cumulative charge (dotted lines) consumed at −400 mV (FIG. 5A) and −500 mV (FIG. 5B) in μmol electron equivalents (μmol eeq) per reactor. Hydrogen accumulation at −400 mV (FIG. 5C) and −500 mV (FIG. 5D) and formate formation at −400 mV (FIG. 5E) and −500 mV (FIG. 5F) are shown in μmol eeq for comparison. Two replicate reactors are shown in different shades of gray and using different symbols to allow identification of each replicate across graphs. The continuous experiment is displayed in two separate parts for reasons of clarity due to the different scales required to display the product formation at different potentials. Diamonds: co-cultures of strain IS4 and A. woodii; triangles: A. woodii pure cultures; circles: un-inoculated controls.
Figure 5B:
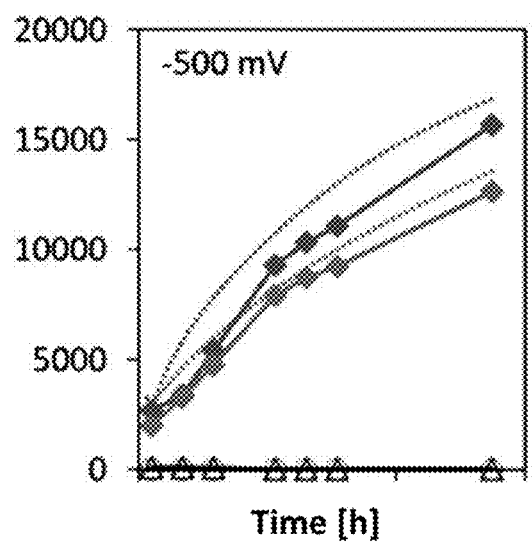
Figure 5C:
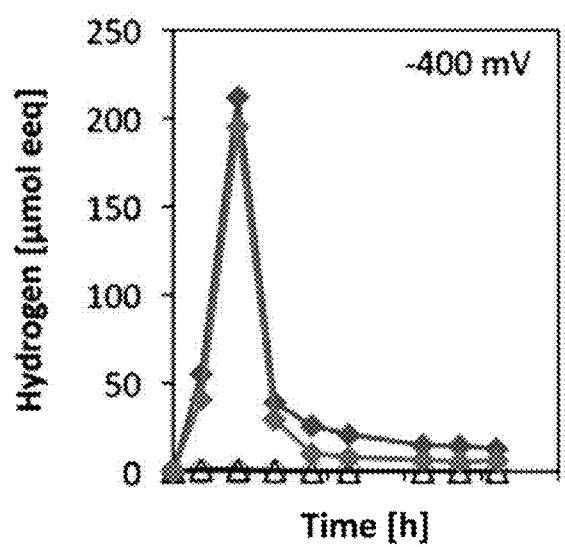
Figure 5D:
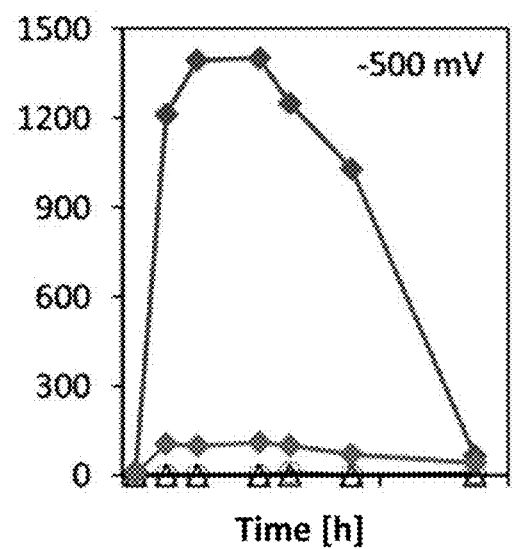
Figure 5E:
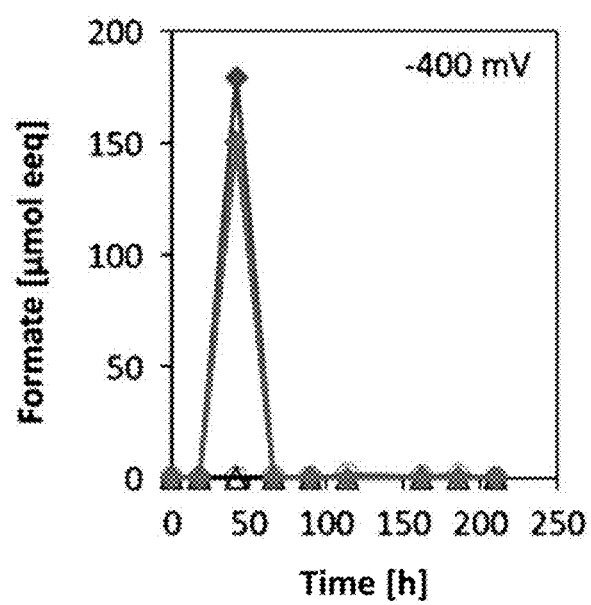
Figure 5F:
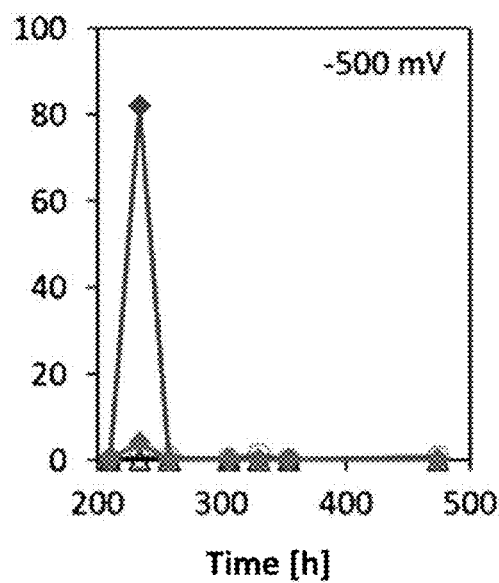

To generalize the finding that a co-culture of strain IS4 and a hydrogenotrophic 'production strain' results in enhanced microbial electrosynthesis, we co-cultured the homoacetogenic bacterium *A. woodii* and strain IS4 in the electrochemical setup. Due to higher concentrations required for experimental detection of acetate (>1 pM), no short-term product formation rates were determined, but we estimated a formation rate from long term incubations. When *A. woodii* cells were added to reactors preincubated with strain IS4, acetate was produced after a lag-phase at rates of 0.21-0.23 pmol $cm^{-2}$ $h^{-1}$ (FIG. 5A). In the lag-phase, hydrogen and formate accumulated transiently and were subsequently consumed correlating with acetate synthesis (FIGS. 5C and 5E). Upon changing the potential to −500 mV, current consumption as well as rate of acetate formation increased significantly to 0.57-0.74 μmol cm-2 $h^{-1}$ (FIG. 5B). Also here, a transient accumulation of formate and hydrogen was observed (FIGS. 5D and 5F). Coulombic efficiencies of acetate formation were low during the initial phase of the co-cultivation, but approached 90% at the end of the incubation. Presumably, the population size of *A. woodii* was insufficient to consume all electron donor generated by strain IS4 at the start of the co-culture and after the decrease of the potential to −500 mV. We surmise that the population size of *A. woodii* adapted to the supply of electron donor via strain IS4 after a few days of incubation. Formate presumably accumulated due to a formate hydrogen lyase activity catalyzed by *A. woodii* (Kantzow and Weuster-Botz (2016) Bioprocess Biosyst. Eng. 39:1325-1330). Acetate synthesis by the co-culture of strain IS4 and *A. woodii* was stable for more than 2 weeks (FIG. 5). Under the conditions used in this study, a pure culture of *A. woodii* was unable to consume current and produce acetate at the potential range investigated.

Discussion $H_2$ Evolution by Microorganisms that Take Up Cathodic Electrons

Our study showed that molecular hydrogen was effectively formed at high rates and in the absence of practically any overpotential at a biocathode containing strain IS4 cells (FIGS. 2 and 3A). Electron uptake and hydrogen evolution rates of the established biocathode were an order of magnitude higher than rates obtained with an abiotic platinum cathode. Comparisons to other inorganic catalysts are difficult, because most catalysts are not evaluated in the potential range suitable for microbial growth. In addition, biofouling of inorganic catalysts and the influence of medium components are not well studied for most inorganic catalysts. As cells attached directly to the electrode surface, and cell-free culture supernatant or cell-free extracts did not catalyze $H_2$ formation (data not shown), cathodic electron uptake is likely not facilitated by cathode-sorbed enzymes as demonstrated in *M. maripaludis* (Deutzmann et al., supra). The findings on electron uptake by Fe(0)-corroding microorganisms such as strain IS4 suggest that these microbes are obvious candidates for mediating the initial biological uptake of cathodic electrons with several fundamental and technological implications.

The high rate of $H_2$ formation from $H^+$ and electrons by strain IS4 at −400 mV corresponds to a high cellular electron uptake rate of $10^6$-$10^7$ $e^-$ $s^{-1}$ $cell^{-1}$ based on estimated cell counts obtained by electron microscopy in this study. These rates agree well with electron uptake rates of $6·10^6$-$1.5·10^7$ $e^-$ $s^{-1}$ $cell^{-1}$ estimated from $H_2$ formation from elemental Fe measured with washed strain IS4 cells (Enning, 2012). Another Fe(0)-corroding microorganism, the methanogenic archaeon strain IM1 was also shown to take up electrons at a high rate of $6·10^6$ and $6·10^7$ $e^-$ $s^{-1}$ $cell^{-1}$ at −400 and −600 mV, respectively (Beese-Vasbender et al. (2015) Bioelectrochemistry 102:50-55). Interestingly, these rates are roughly in the same order of magnitude as the single cell anodic reduction reaction in *Shewanella oneidensis* ($10^5$-$10^6$ $e^-$ $s^{-1}$ $cell^{-1}$) (Gross and El-Naggar (2015) Rev. Sci. Instrum. 86: 064301). Notably, only some Fe(0) corroding strains form hydrogen from cathodic electrons while other strains such as strain IS5 do not accumulate hydrogen (Dinh et al., supra). Therefore, only $H_2$ producing strains, including strain IS4, represent a promising biocatalyst for the generation of $H_2$ at a cathodic surface. Another benefit of using sulfate reducers lies in the fact that growth of the microorganism can be controlled by limiting the sulfate concentration in the reactor solution. Thus, during the electrosynthesis phase, only a negligible fraction of the electrical energy and electrons are directed towards biomass production of strain IS4, and the coulombic efficiency of hydrogen formation can achieve values of close to 100%. Thus, during long-term operation a continuous or batch fed system with additions of small amounts of sulfate could sustain a stable population of strain IS4 thriving on sulfate reduction while slowly re-supplying a reduced sulfur source for anaerobic microorganisms unable to assimilate sulfate. During continuous operation at neutral pH, the gas stream will slowly strip sulfide out of solution and, thus, deplete the sulfur source.

Due to the differences in the reporting of product formation rates in the literature (for example, as specific rate per electrode surface area, reactor volume or total amount per reactor), associated projected areal current densities are used in this study for normalization to allow direct comparisons. However, faradaic efficiencies are not always reported and, thus, projected areal current densities might slightly overestimate actual product formation rates. Current densities of 1.1-3.3 A $m^{-2}$ at −700 mV were reported during hydrogen formation using mixed cultures in microbial electrolysis cells (Rozendal et al. (2008) Environ. Sci. Technol. 42:629-634; Jeremiasse et al. (2010) Bioelectrochemistry 78:39-43; Croese et al. (2011) Appl. Microbiol. Biotechnol. 92:1083-1093; Jeremiasse et al. (2012) Biotechnol. Bioeng. 109:657-664), and current densities of 0.76 A $m^{-2}$ were measured using a pure culture of the non-corroding sulfate reducer *Desulfovibrio* G11 (Croese et al., supra). In our study, strain IS4 achieved similar current densities of 1.5 A $m^{-2}$ already at a cathode potential of −500 mV and, thus, at a potential 200 mV more positive than in previously published studies. In addition, we used plain graphite electrodes which likely provide a lower effective surface area than graphite felt electrodes used in other studies (Rozendal et al. (2008) Environ. Sci. Technol. 42:629-634; Jeremiasse et al. (2010) Bioelectrochemistry 78:39-43; Croese et al., supra; Jeremiasse et al. (2012) Biotechnol. Bioeng. 109:657-664). Besides electrode surface area, the cell density on the electrode surface impacts overall electron transfer rates. However, all isolates described to perform electrical microbially influenced corrosion, including strain IS4, do not form thick biofilms but form dispersed patchy monolayers of cells (Beese-Vasbender et al. (2015) Bioelectrochemistry 102:50-55, Beese-Vasbender et al. (2015) Electrochimica Acta 167: 321-329). Thus, improving attachment and biofilm growth of these strains might greatly increase areal current densities and should be addressed in future research.

Efficient Interspecies Hydrogen Transfer in Mixed Electrosynthetic Cultures

The rates of electromethanogenesis by a co-culture of strain IS4 and *M. maripaludis* presented here are the highest reported to date. Compared with a recent study using *Methanobacterium* strain IM1 (Beese-Vasbender et al. (2015) Bioelectrochemistry 102:50-55), methanogenesis rates reported here were about one order of magnitude higher at −400 mV (100-140 nmol $h^{-1}$ $cm^{-2}$ compared with 12-14 nmol $h^{-1}$ $cm^{-2}$ in (Beese-Vasbender et al. (2015) Bioelectrochemistry 102:50-55). However, electron uptake rates were comparable between both studies, and molecular hydrogen was likely a side product during electromethanogenesis by strain IM1, which became obvious at more negative potentials (Beese-Vasbender et al. (2015) Bioelectrochemistry 102:50-55). The rates obtained here with the co-culture are about 20 times higher compared with electromethanogenesis using axenic *M. maripaludis* at −600 mV (Lohner et al. (2014) ISME J 8: 1673-1681) (0.6-1.2 μmol $h^{-1}$ $cm^{-2}$ compared with 0.05 μmol $h^{-1}$ $cm^{-2}$). In addition, the overpotential for electromethanogenesis by the co-culture was >200 mV lower, thus resulting in less energy loss in this cathodic reaction. Few studies have shown microbial electrosynthesis of acetate, butanol or other multi-carbon compounds by pure cultures of homoacetogenic microorganisms. Electron transfer rates at a potential of −400 mV in these systems varied between strains and ranged from no electron uptake using *A. woodii* to 0.01 A $m^{-2}$ using *Moorella thermoacetica* and to 0.2 A $m^{-2}$ using *Sporomusa ovata* (Nevin et al. (2010) MBio 1:e00103-e00110, Nevin et al. (2011) Appl. Environ. Microbiol. 77:2882-2886). Thus, the electron uptake rates achieved by our co-culture of strain IS4 with *A. woodii* (0.2-0.5 A $m^{-2}$ at −400 mV) are slightly higher than the rates published with pure cultures of homoacetogens (Nevin et al. (2011), supra). Other studies using mixed cultures achieved high electro-synthesis rates when applying large overpotentials (3-20 A $m^{-2}$ at −800 mV, (Ganigue et al. (2015) Chem. Commun. 51: 3235-3238) at which the apparent 'electro' synthetic activity is most likely due to the abiotic formation of hydrogen. At the cost of high overpotentials and higher energy losses, hydrogen is formed under these conditions even at electrodes with low catalytic activity for $H_2$ evolution. This overpotential can be reduced when cell-derived enzymes or cofactors adsorb to the surface (Yates et al. (2014) Int. J. Hydrogen Energ. 39:16841-16851; Deutzmann et al. (2015) Mbio 6:e00496-15). In our defined co-culture, hydrogen was formed already at −400 mV, which enabled electrosynthesis with *A. woodii* that has been shown previously to be unable to carry out electrosynthesis (Nevin et al. (2011), supra) due to efficient interspecies hydrogen transfer.

General Benefits of a Decoupled Microbial Electron Uptake—Microbial Synthesis System In a microbial electrosynthesis system, the combination of an efficient electron uptake step with an efficient synthesis step of a compound of interest has several distinct advantages over a single microorganism process: (1) It becomes possible to engineer and operate two fundamentally different metabolic processes independently. Each microorganism can be optimized for its purpose, for example, through genetic engineering, without the need to consider additional tradeoffs imposed by the other process, and there are numerous efforts to engineer homo-acetogenic microorganisms to produce, for example, ethanol, butanol and isobutanol (Köpke et al. (2010) Proc. Natl. Acad. Sci. USA 107:13087-13092; Leang et al. (2013) Environ. Microbiol. 79:1102-1109; Banerjee et al. (2014) Appl. Environ. Microbiol. 80:2410-2416; Cho et al. (2015) Biofuels, Bioprod. Biorefin. 9:211-225); (2) Only the electron uptaking strain has to contact the cathode while end product formation can proceed in the bulk liquid, which allows better use of the volume of the cathode compartment; (3) two microbial organisms adapt to each other's metabolic capabilities via a thermodynamic-kinetic feedback loop resulting in an optimized metabolic flux without accumulation of intermediates. In addition, mixed communities are often reported to show higher electron transfer rates or higher current efficiencies than pure cultures (Dinh et al., supra; Nevin et al. (2008) Environ. Microbiol. 10:2505-2514; Call et al. (2009) Appl. Environ. Microbiol. 75:7579-7587; Fast and Papoutsakis (2012) Curr. Opin. Chem. Eng. 1:380-395; Ganigue et al. (2015) Chem. Commun. 51:3235-3238). Thus, especially with the possibility to engineer and improve each specialist in the co-culture, a stable and probably faster electrosynthesis system can be achieved compared with engineering existing iron corroding methanogens or homoacetogens (Uchiyama et al. (2010) Appl. Environ. Microbiol 76:1783-1788; Kato et al. (2015) Appl. Environ. Microbiol. 81:67-73).

Electron Uptake Strains as Ecosystem Engineers in Cathodic Communities

Our finding that electrosynthesis rates can be improved substantially by co-cultivating an electron uptake strain that produces hydrogen with hydrogenotrophic strains prompts the question about the ecological relevance of such strains and their role in more natural environments. Successful co-cultivation of strain IS4 with a homoacetogen and a methanogen shows that interspecies hydrogen transfer can effectively distribute cathodic electrons to microorganisms that by themselves do not have the capacity for direct electron uptake. According to Jones, organisms directly or indirectly modulating the availability of resources (other than themselves) to other species by causing state changes in biotic or abiotic materials are called 'ecosystem engineers' in ecology (Jones et al. (1994) Oikos 69:373-386). Microbial strains that facilitate electron uptake from a cathodic surface and supply electrons to the surrounding community can, therefore, be considered ecosystem engineers. Although this possibility has already been mentioned in one of the first studies on electrosynthesis by mixed species biofilms (Marshall et al. (2012) Appl. Environ. Microbiol. 78:8412-8420), it lacked evidence for single strains catalyzing hydrogen formation at a high rate. Based on the high cellular electron uptake rates ($>10^6$ $e^-$ $s^{-1}$ $cell^{-1}$), even a relatively small number of electroactive cells could result in substantial current consumption rates and thereby provide an effective electron donor for a diverse microbial ecosystem. Accordingly, the hydrogen evolution rate of a single strain IS4 cell (up to 30 fmol $h^{-1}$) would be sufficient to supply all the hydrogen consumed by one *M. maripaludis* cell under optimum growth conditions (2 hour doubling time), and provides hydrogen at a rate an order of magnitude higher than hydrogen uptake rates of other more slowly growing organisms (Goyal et al. (2015) Microb. Cell Fact. 14:146). Besides intact cells that transform cathodic electrons into a widely accessible substrate, such as hydrogen, strains that release electroactive enzymes such as hydrogenases have to be considered in cathodic communities. Even small amounts of electrocatalytically active enzymes could be sufficient to sustain biofilms on a cathodic surface due to the high turnover rates of hydrogenases.

Examples for candidate strains ('ecosystem engineers') mediating the key electron uptake to support complex cathodic biofilms can be found in the literature. The genus *Methanobacterium* became enriched in several studies investigating electro-methanogenesis (Pozo et al. (2015) RSC Advances 5:89368-89374; Siegert et al. (2015) ACS Sustain Chem. Eng. 3:1668-1676) and it has been shown in pure culture that *Methanobacterium* strain IM1 not only catalyzed electrosynthetic methanogenesis but also accumulated hydrogen during electromethanogenesis (Beese-Vasbender et al. (2015) Bioelectrochemistry 102:50-55), which can create a niche for other microorganisms. In homoacetogenic communities, the role of distinct electron uptake strains seems to be more elusive. A variety of homoacetogenic bacteria were shown to use cathodic electrons in pure culture (Nevin et al. (2010), supra, Nevin et al. (2011), supra). However, in acetate-producing electrosynthesis reactors inoculated with undefined mixed cultures the cathode-associated community was often dominated by *Acetobacterium* spp., which had been reported to lack the ability to utilize cathodic electrons (Nevin et al. (2011), supra). Often, sulfate reducers such as *Desulfovibrio* sp. are also present in these enrichments (Marshall et al. (2013) Environ. Sci. Technol. 47:6023-6029; LaBelle et al. (2014) PloS One 9:e109935; Patil et al. (2015) Environ. Sci. Technol. 49:8833-8843), suggesting that hydrogen produced by the sulfate reducers might have a role in these biofilms. However, the role of individual strains in mixed communities and the molecular mechanism of microbial electron uptake from the cathode are unclear in most cases. Thus, further research is needed on the electron uptake mechanism(s) acting in different electron uptake strains and identification of these key 'ecosystem engineers'.

In summary, this study shows that an electro-synthesis system relying on interspecies hydrogen transfer is able to outperform mono-culture electro-methanogenesis based on direct electron transfer and it emphasizes the importance of an efficient biological hydrogen evolution step for effective electro-synthesis for example, using *M. maripaludis*. Furthermore, certain microbial strains can transmute cathodic electrons to reduced diffusible compounds such as hydrogen at rates exceeding their own metabolic capacity to use these compounds. As a consequence, these compounds become available as substrates to other hydrogenotrophic strains and could potentially sustain a diverse cathodic biofilm. Thus, defined co-cultures may represent a foundation for an engineering strategy for microbial electrosynthesis and provide a means to understand complex cathodic biofilms.

Although preferred embodiments of the subject invention have been described in some detail, it is understood that obvious variations can be made without departing from the spirit and the scope of the invention as defined herein.

What is claimed is:

1. A microbial electrosynthesis system comprising:
    a) a cathode;
    b) an anode;
    c) a power supply electrically connected to the cathode and the anode;
    d) a first microorganism attached to the cathode, wherein the first microorganism is selected from the group consisting of a *Desulfopila* bacterium, a *Geobacter* bacterium, and a *Desulfovibrio* bacterium, wherein the first microorganism comprises a hydrogenase that is capable of accepting electrons derived from the cathode resulting in reduction of protons to produce hydrogen or a formate dehydrogenase or a formate-hydrogen lyase that is capable of accepting electrons derived from the cathode resulting in reduction of carbon dioxide to produce formate when the cathode is at a suitable negative potential;
    e) a second microorganism in sufficient proximity to the first microorganism to allow consumption of the hydrogen or the formate generated by the first microorganism, wherein the second microorganism is capable of biosynthesis of an organic compound of interest from carbon dioxide and the hydrogen or the formate generated by the first microorganism; and
    f) media suitable for growth or metabolic activity of the first microorganism and the second microorganism; and
    g) carbon dioxide.

2. The microbial electrosynthesis system of claim 1, wherein the cathode is composed of a biocompatible material.

3. The microbial electrosynthesis system of claim 2, wherein the biocompatible material comprises graphite or other conductive carbon material, indium tin oxide (ITO), fluorine-doped tin oxide (FTO), platinum, titanium, silver, or gold, or a metal alloy or an oxide comprising at least one of tin, platinum, titanium, silver, or gold.

4. The microbial electrosynthesis system of claim 1, further comprising a chamber, wherein the second microorganism is inside the chamber.

5. The microbial electrosynthesis system of claim 4, wherein the anode and the cathode are inside the chamber.

6. The microbial electrosynthesis system of claim 1, further comprising a first chamber comprising the cathode and a second chamber comprising the anode.

7. The microbial electrosynthesis system of claim 6, wherein the first microorganism and the second microorganism are inside the first chamber comprising the cathode.

8. The microbial electrosynthesis system of claim 6, further comprising a membrane separating the first chamber and the second chamber.

9. The microbial electrosynthesis system of claim 8, wherein the membrane allows proton exchange, cation exchange, or anion exchange between the first chamber and the second chamber.

10. The microbial electrosynthesis system of claim 8, wherein the membrane is a bipolar membrane.

11. The microbial electrosynthesis system of claim 1, wherein the second microorganism is a bacterium or an archaeon.

12. The microbial electrosynthesis system of claim 1, wherein the *Desulfopila* bacterium is *Desulfopila corrodens*.

13. The microbial electrosynthesis system of claim 12, wherein the *Desulfopila corrodens* bacterium is strain IS4.

14. The microbial electrosynthesis system of claim 12, wherein the hydrogen producing microorganism is a sulfate-reducing bacterium.

15. The microbial electrosynthesis system of claim 1, wherein the hydrogen producing microorganism is an iron-corroding bacterium.

16. The microbial electrosynthesis system of claim 1, wherein the second microorganism is a hydrogenotrophic microorganism.

17. The microbial electrosynthesis system of claim 1, wherein the second microorganism is a methanogen or an acetogen.

18. The microbial electrosynthesis system of claim 17, wherein the methanogen is selected from the group consisting of *Methanobacteriales, Methanocellales, Methanococcales, Methanomicrobiales, Methanosarcinales*, and *Methanopyrales* archaea.

19. The microbial electrosynthesis system of claim 18, wherein the first microorganism is *Desulfopila corrodens* strain IS4 and the methanogen is *Methanococcus maripaludis*.

20. The microbial electrosynthesis system of claim 17, wherein the acetogen is selected from the group consisting of *Acetobacterium, Moorella, Thermoanaerobacter, Thermacetogenium, Clostridium*, and *Bathyarchaeota* acetogens.

21. The microbial electrosynthesis system of claim 20, wherein the first microorganism is *Desulfopila corrodens* strain IS4 and the acetogen is *Acetobacterium woodii*.

22. A method of microbial electrosynthesis comprising:
    a) cultivating the first microorganism on the cathode in the microbial electrosynthesis system of claim 1;
    b) applying a voltage with the power supply such that an electron is transferred from the cathode to the first microorganism, wherein the reduction of protons results in formation of the hydrogen or wherein the reduction of carbon dioxide results in formation of the formate by the first microorganism;
    c) cultivating the second microorganism in sufficient proximity to the first microorganism to allow consumption of the hydrogen or the formate by the second microorganism; and
    d) providing carbon dioxide to the second microorganism, wherein the second microorganism metabolizes the carbon dioxide and the hydrogen or the formate resulting in production of the organic compound of interest.

23. The method of claim 22, wherein the first microorganism or the second microorganism is a bacterium or an archaeon.

24. The method of claim 22, wherein the desired organic compound is methane or acetate.

25. The method of claim 22, wherein the second microorganism produces an alcohol.

26. The method of claim 22, wherein the second microorganism is engineered to produce a desired organic compound.

27. The method of claim 22, wherein the first microorganism is supplied with growth media using a continuous or batch fed system.

28. The method of claim 27, wherein supply of the growth media to the first microorganism is controlled to limit its cell density to between about $10^7$ to about $10^8$ cells $cm^{-2}$ on the cathode surface.

29. The method of claim 22, wherein the cathode is at a voltage ranging from about −400 mV to about −500 mV.

30. The method of claim 22, wherein the hydrogen is generated by the first microorganism at a rate of at least 0.4 pmol $cm^{-2}$ $h^{-1}$.

31. The method of claim 30, wherein the hydrogen is generated by the first microorganism at a rate ranging from 4 pmol $cm^{-2}$ $h^{-1}$ to 7 pmol $cm^{-2}$ $h^{-1}$.

32. The method of claim 22, wherein the hydrogen is generated from cathodic electrons at a coulombic efficiency of at least 90%.

33. The microbial electrosynthesis system of claim 1, wherein the cathode is at a cathode potential ranging from about −400 mV to about −500 mV versus a standard hydrogen electrode.

34. The microbial electrosynthesis system of claim 1, wherein the carbon dioxide is supplied to the first microorganism if the first microorganism comprises the formate dehydrogenase or the formate-hydrogen lyase to allow the production of the formate, and the carbon dioxide is supplied to the second microorganism for the biosynthesis of the organic compound of interest.

* * * * *